United States Patent [19]
Bennett et al.

[11] Patent Number: 5,331,966
[45] Date of Patent: Jul. 26, 1994

[54] SUBCUTANEOUS MULTI-ELECTRODE SENSING SYSTEM, METHOD AND PACER

[75] Inventors: Tom D. Bennett, Shoreview; William J. Combs, Eden Prairie; Kallok, Michael J., New Brighton; Brian B. Lee, Golden Valley; Rahul Mehra, Stillwater, all of Minn.; George J. Klein, London, Canada

[73] Assignee: Medtronic, Inc., Minneapolis, Minn.

[21] Appl. No.: 168,725

[22] Filed: Dec. 16, 1993

Related U.S. Application Data

[63] Continuation of Ser. No. 70,008, May 28, 1993, abandoned, which is a continuation of Ser. No. 681,235, Apr. 5, 1991, abandoned.

[51] Int. Cl.⁵ ............................................. A61B 5/0428
[52] U.S. Cl. ...................................... 128/696; 128/903; 607/28
[58] Field of Search ............... 128/642, 696, 697, 903; 607/9, 28

[56] References Cited

U.S. PATENT DOCUMENTS 4,365,639 12/1982 Goldreyer ........................... 128/786
4,686,988 8/1987 Sholder ............................... 128/419
5,135,004 8/1992 Adams ................................ 128/696

Primary Examiner—William E. Kamm
Attorney, Agent, or Firm—Reed A. Duthler; Harold R. Patton

[57] ABSTRACT

A method and apparatus for providing an enhanced capability of detecting and gathering electrical cardiac signals via an array of relatively closely spaced subcutaneous electrodes (located on the body of an implanted device) which may be employed with suitable switching circuits, signal processors, and memory to process the electrical cardiac signals between any selected pair or pairs of the electrode array in order to provide a leadless, orientation insensitive means for receiving the electrical signal from the heart. This far-field EGM may be used to provide storage and analysis of arrhythmic events and to provide control signals for the delivery of various therapies including pacing, cardioversion and defibrillation therapies as well as the delivery of antiarrhythmic drugs, and, in the pacing context, to effect capture detection and automatic stimulation threshold adaption, recording of PMT episodes, measurement of refractory periods in order to set timing windows for antitachy pacing therapies, and as a control signal for use in adjusting pacing rate to physiologic demand.

29 Claims, 18 Drawing Sheets

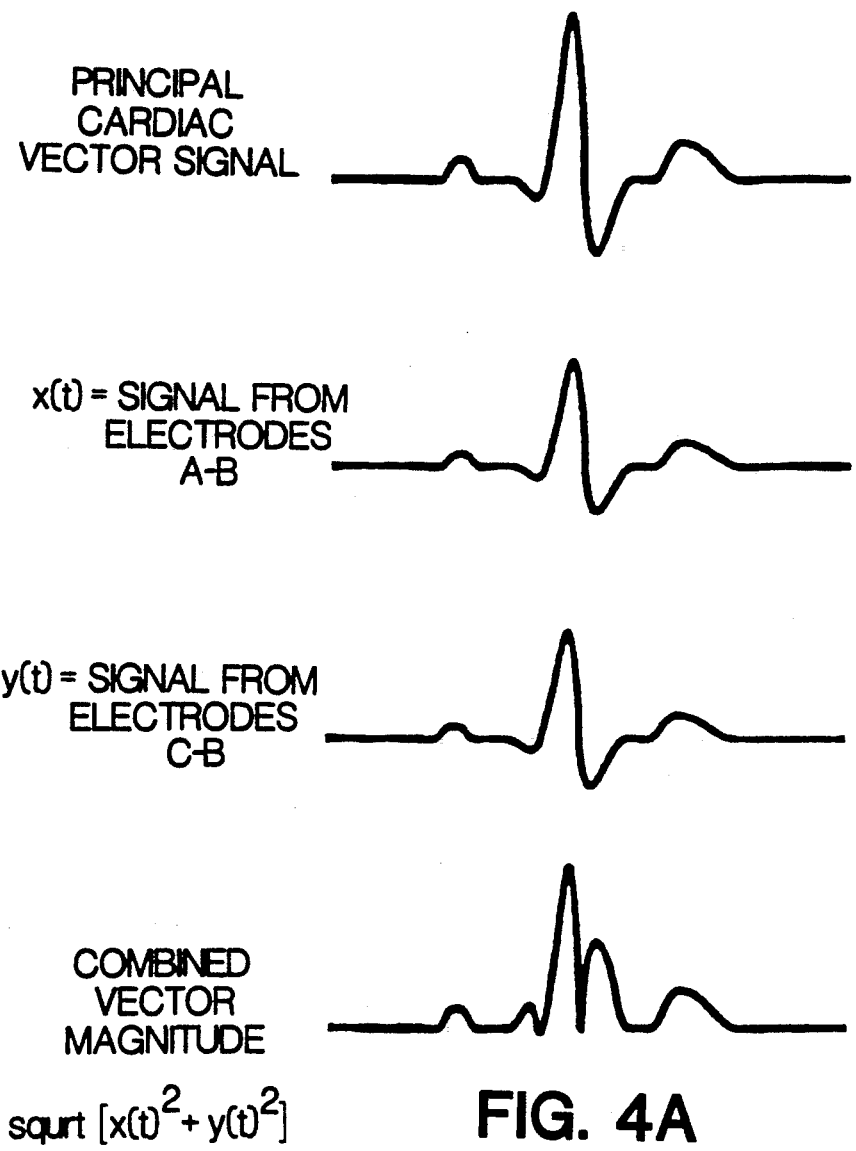

SUBCUTANEOUS MULTI-ELECTRODE SENSING SYSTEM, METHOD AND PACER

This application is a continuation of U.S. patent application Ser. No. 08/070,008, filed May 28, 1993, now abandoned, which in turn was a continuation of U.S. patent application Ser. No. 07/681,235, filed Apr. 5, 1991, now abandoned.

BACKGROUND OF THE INVENTION

1. Field of the Invention

The present invention generally relates to implanted medical devices, and more particularly, pertains to a subcutaneous multiple electrode sensing recording and control system for an implanted cardiac pacemaker, pacemaker-cardioverter-defibrillator, drug administration device, or cardiac monitoring device.

2. Description of the Prior Art

Cardiac Arrhythmia Control Devices—Since the implantation of the first cardiac pacemaker, implantable medical device technology has advanced with the development of sophisticated, programmable cardiac pacemakers, pacemaker-cardioverter-defibrillator arrhythmia control devices and drug administration devices designed to detect arrhythmias and apply appropriate therapies. The detection and discrimination between various arrhythmic episodes in order to trigger the delivery of an appropriate therapy is of considerable current interest. Arrhythmia detection and discrimination algorithms are based in the analysis of the PQRST electrogram (EGM), usually separated for such analysis into the P-wave and R-wave, in systems which are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices is well known in the art.

The cardiac arrhythmias which have been treated by the aforementioned medical devices constitute variations in heart rate from the normal sinus rate range of approximately 60 to 120 beats per minute prevalent in healthy adult humans with normally functioning hearts in light to moderate exercise ranges. Bradycardia is typically characterized by rates below 60 beats per minute, although extreme bradycardia resulting in the absence of heart beat for a time sufficient to render the patient unconscious is referred to as syncope. Rates exceed about 120 beats per minute are typically characterized as tachycardia and are usually experienced as a result of such factors as physical exercise, emotional stress, pathologic cardiac disease and side effects of drugs that elevate heart rate. The normal acceleration of heart heart above 120 beats per minute in conjunction with moderate to heavy exercise is referred to as sinus tachycardia and is characterized by gradual acceleration in heart rate with normal P-wave and R-wave morphology. Tachyarrhythmias, on the other hand, are characterized by an increase in rate above 120 beats per minute not accompanied necessarily by physical exercise or emotional stress and are often accompanied by herald signs including ectopic ventricular depolarizations, unnatural morphologies and sudden onset rate increase. Such atrial or ventricular tachycardias also often spontaneously subside whereas sinus tachycardia exhibits a gradual slow down in rate with a cessation of exercise or emotional stress.

Life threatening tachyarrhythmias which require special medical treatment include high rate ventricular tachycardias and ventricular fibrillation. High rate ventricular tachycardias are characterized by fairly regular but wide morphology accompanied by some degree of hemodynamic compromise. Ventricular fibrillation is a life threatening tachyarrhythmia characterized by completely uncoordinated contractions of sections of conductive cardiac tissue of the affected chamber of the heart, resulting in a complete loss of synchronous contraction of the overall heart mass. As a consequence, the chamber ceases to pump blood effectively and in the case of ventricular fibrillation, the lack of oxygenated blood to the tissues will lead to death within minutes. Such sudden death if encountered in the hospital situation is treated by the application of cardioversion or defibrillation shock therapy. High rate atrial tachycardias and atrial fibrillation are less life threatening and patients normally recover from such episodes. However, the recurrence is suspected as a precursor to the development of life threatening ventricular arrhythmias.

In the case of the patient suffering from syncope, Stokes-Adams syndrome, sick sinus syndrome and a host of other brady/tachyarrhythmias, the preferred choice for treatment involves the implantation of a cardiac pacemaker having the capability of detecting the brady and/or tachyarrhythmia and applying pacing impulses to the heart to stimulate it to beat at a desired rate in the normal sinus range or to stimulate it at a certain high rate to treat tachycardias. In the management of tachyarrhythmia, the heart may be artificially stimulated at a faster than normal pacing rate to terminate the tachycardia or suppress premature atrial ventricular contractions which could otherwise lead to supraventricular or ventricular tachycardia, flutter or fibrillation. The pulses delivered to the heart for pacing therapy need only be of sufficient magnitude to stimulate the excitable myocardial tissue in the immediate vicinity of a pacing electrode.

More recently, the automatic pacer-cardioverter-defibrillator has been implanted in cardiac patients prone to suffer ventricular tachycardia and/or fibrillation. In such devices the functions of bradycardia and antitachycardia pacing type therapies, and cardioversion and defibrillation shock type therapies, are integrated to provide a coordinated approach to the management and treatment of ventricular arrhythmias. In such devices, therapy regimens may be programmed for the treatment of arrhythmic episodes, and the resulting successful treatment successes and failures are recorded for later analysis. In such systems, sophisticated detection algorithms for discriminating tachyarrhythmias from sinus tachycardia episodes have been proposed and implemented. The detection and discrimination of arrhythmic episode remains a subject of considerable interest inasmuch as the failure to properly discriminate may lead to the misapplication of therapies to the patient's detriment and leading to the early depletion of the implanted device's power source.

In this regard, it has also been proposed to record data upon which the detection algorithm acted in prescribing a certain therapy. Such data may include the measured interval between successive P-waves and/or R-waves, sequences of such intervals, and/or sequences of actual sampled EGMs from a point in time prior to the satisfaction of the detection algorithm to a point in time thereafter. The storage of such data has been facilitated by the implementation of microprocessor based signal processing and control systems with recirculating buffers for receiving such data and dedicated RAM into which the buffered data may be transferred. Such data may be read out at a later time by interrogation of the contents of the RAM through the use of uplink and downlink telemetry between the implanted device and an external programmer/transceiver.

It has also been proposed that implantable drug administration devices be developed as a substitute for or to augment the aforementioned brady and tachyarrhythmia control stimulation devices. In such systems, it has been proposed that antiarrhythmic drugs be delivered systemically where appropriate upon detection of the arrhythmic episodes or upon detection of other cardiac dysfunctions, such as elevated or depressed blood pressure. With the advent of chronically implantable blood-gas sensors, blood pressure sensors, mechanical activity sensors, and the like, such systems for the combined detection analysis and therapeutic treatment of various cardiac malfunctions appear to be realizable.

The aforementioned systems which depend on detection and analysis of the PQRST complex are all dependent upon the spatial orientation and number of electrodes available in or around the heart to pick up the depolarization wave front. Within the bradycardia pacing system context, it has been customary to employ pace/sense electrode pairs for detecting P-waves and R-waves and stimulating the atrium and ventricle. As described hereinafter, such pacing systems are limited in their capabilities of detecting the "capture" of the patient's heart by a pacing pulse and in detecting and storing EGM episodes of syncope, spontaneous tachycardia or pacemaker mediated tachycardia. Similarly, pacemaker-cardioverter-defibrillator arrhythmic control devices and implantable drug administration devices would benefit from enhanced capabilities of discriminating arrhythmias and storing data associated therewith.

Unipolar/Bipolar Leads—From the early days of pacing, two varieties of electrode configurations have been used for both pacing and sensing, namely unipolar and bipolar. Whether the pacemaker is called unipolar or bipolar depends on the location of both electrodes relative to the pacemaker and the heart. The unipolar and bipolar nomenclature is also applied in the pacemaker-cardioverter-defibrillator context, although bipolar and unipolar sensing may also be referred to as "near-field" and "far-field" sensing, respectively.

The unipolar electrode configuration has one pole or electrode (i.e., cathode electrode or negative pole) located on or within the heart, and the other pole (i.e., anode electrode or positive pole) remotely located from the heart. With endocardial leads, for example, the cathode is located at the distal end of the lead and typically in direct contact with the endocardial tissue to be stimulated, thus forming a "tip" electrode. Conversely, the anode is remotely located from the heart, such as comprising a portion of the metallic enclosure which surrounds the implanted device, thus forming a "can" electrode and is often referred to as the "indifferent" electrode.

The bipolar electrode configuration has both poles or electrodes typically located within the atrial or ventricular chamber of the heart. With endocardial leads, for example, the cathode is located at the distal end of the lead, again referred to as the "tip" electrode. In the bipolar configuration, the anode is usually located proximal to the "tip" electrode, spaced apart by 0.5 to 2.5 cm., and typically forming a ring-like structure, referred to as the "ring" electrode.

A variety of lead configurations can be used to pace the heart and sense its depolarizations (whether intrinsic or evoked). Atrial unipolar or bipolar electrode configurations, as well as ventricular unipolar or bipolar electrode configurations, have been used to pace the heart.

With respect to sensing, it is well known that bipolar and unipolar electrode configurations do not yield equivalent cardiac electrograms. Each configuration has advantages and disadvantages. With a unipolar sensing configuration, for example, only the electrical events adjacent to the "tip" electrode control the unipolar electrogram, while the remote "indifferent" electrode contributes negligible voltage due to its location being extracardiac.

With a bipolar sensing configuration, the magnitude of the cardiac signal will be similar for both the "ring" and "tip" electrodes, but the resulting electrogram will be highly dependent upon the orientation of the electrodes within the heart. Optimal sensing will occur, for example, when the sensing vector defined by the sensing electrodes is parallel with the dipole defined by the depolarization signal. Since bipolar electrodes are more closely spaced than their unipolar counterparts, the depolarization signal will be shorter in duration than that produced from a unipolar configuration. Due to a more restricted lead field or antenna, bipolar sensing offers improved rejection of electromagnetic and skeletal muscle artifacts and thus provides a better signal-to-noise ratio than unipolar sensing.

Post-Stimulus Residual Electrode Polarization—The delivery of an electrical stimulus to cardiac tissue induces a field which is generally orders of magnitude greater in amplitude that the field caused by the electrical activity of the tissue itself. When the stimulus ends, electrical fields remain in tissue primarily due to two factors. The first factor relates to the electrochemical equilibrium at the electrode-tissue interfaces, which has been disturbed by the stimulus, and has to reestablish itself. The second factor relates to the function of the pacemaker's output capacitor being recharged through its electrical circuits, which involve the heart as well.

When the same electrodes are used as pacing electrodes to stimulate myocardial contraction and as sensing electrodes to detect the resulting depolarization, detection of depolarization is typically somewhat reduced, because it is masked or buried in the exponential decay of the residual polarization charge on the electrode resulting from the stimulation pulse itself.

U.S. Pat. No. 4,406,286 to Stein relates to a pacemaker having an R-wave capture detection capability in which the same electrodes are utilized for both pacing and sensing (i.e., unipolar or bipolar), and wherein a bipbasic pulse is delivered for purposes of dissipating the polarization charge on the pacing electrode. The first phase is of relatively shorter duration and greater amplitude than the second phase for purposes of stimulating the myocardium, while the second phase is of relatively longer duration, lesser amplitude and opposite polarity than the first phase for purposes of providing charge compensation to neutralize the undesired electrode polarization, following which the capture detection sensing amplifier is turned on. Such "fast recharge" wave forms have been employed for many years in an attempt to facilitate short blanking and refractory time intervals following stimulation.

Limitations of Sense Amplifiers—Conventional sensing circuitry cannot be used to detect the electrogram immediately following a stimulation pulse. The relatively high output pulse, after-potentials, and electrode-tissue polarizations render the electrode blind to the induced electrogram. Since the sensing circuit gain is tuned for the relatively low voltages of the heart (i.e., 3 to 4 mV for the atrium, and 10 to 20 mV for the ventricle), the significantly greater output levels produced by the stimulation pulse (i.e., varying between 1 to 8 V) must be blocked from the sensing circuit by blanking and refractory periods so that the pacemaker is not adversely affected.

Thus, it is conventional to suppress or blank the sensing amplifier during a stimulus to avoid overloading. However, when blanking is over and the sense amplifier is reconnected, the sense amplifier may abruptly sense a different potential than was present at the time of initial blanking, due to the after-potentials and electrode polarization as well as the recharge function, all of which can produce unwanted artifacts in the sensing signal.

"Capture" Defined—Capture is defined as an evoked cardiac response to a pacemaker output or stimulation pulse. In a pacemaker with dual-chamber pacing capabilities, for example, a stimulation pulse can be applied to either the heart's atrium or the ventricle during an appropriate portion of a cardiac cycle. The minimum output pulse energy which is required to capture and thus evoke a muscular depolarization within the heart is referred to as the stimulation threshold, and generally varies in accordance with the well known strength-duration curves, wherein the amplitude of a stimulation threshold current pulse and its duration are inversely proportional.

A number of factors can influence changes in the stimulation threshold for each patient, however, following implantation of the pacemaker and pacing lead. Factors which can influence both acute and chronic stimulation thresholds include, for example: (1) changes in position of the pacing electrode relative to the cardiac tissue; (2) long-term biologic changes in cardiac tissue closely adjacent the electrode, such as due to fibrotic tissue ingrowth; (3) changes in the patient's sensitivity to stimulation as a function of periodically fluctuating conditions, even on a daily basis, due to various causes such as diet, exercise, administered drugs, electrolyte changes, etc.; and (4) gradual changes in pacemaker/lead performance due to various causes such as battery depletion, component aging, etc.

Capture Detection and Adjustable Output Pulse Energy—To conserve battery power and extend the pacemaker's useful life, it is usually desired to achieve capture at the lowest possible energy setting for the output pulse. With the advancement of programmable pacemakers, it became common to initially program an output pulse energy setting which includes a safety margin somewhat above that required to produce capture. These programmable pacemakers include a programmable output stimulation pulse which permits the physician to select an output pulse energy which is known to be sufficient to capture the heart but which is below the maximum obtainable output energy of the pacemaker. Such output pulse energy adjustments are usually accomplished by the attending physician during an office visit with the use of an external programmer and an electrocardiogram (ECG) monitor. At this time, the physician may assess capture by means of an ECG measured through ECG electrodes placed on the patient's limbs and/or chest, during which time the pacemaker is providing a sequence of temporarily programmed-in stimulation pulses with decreasing pulse energies in a system of the type described in U.S. Pat. No. 4,250,884 to Hartlaub, et al. For example, capture detection of the ventricle is confirmed by the presence of the evoked QRS complex or R-wave, and capture detection of the atrium is confirmed by the presence of the evoked P-wave. Loss of capture can be directly observed and correlated to the pulse energy at which capture is lost.

Since the late 1960's, self-adaptive pacemakers have been developed which have the capability of automatically adjusting the energy content of the pacing pulse as appropriate to accommodate changes in stimulation threshold.

U.S. Pat. No. 3,757,792 to Mulier et al, for example, relates to an early pacemaker which provides for a decreased battery drain by sensing each driven heart beat (i.e., R-wave) and providing for a decrease in energy for each succeeding output pulse until such time as loss of capture is detected. Following a detected loss of capture, the next succeeding output pulse is increased in energy by an amount to be safely over the threshold hysteresis level. U.S. Pat. No. 3,949,758 to Jirak (incorporated herein by reference) relates to a similar threshold-seeking pacemaker with automatically adjusted energy levels for output pulses in response to detected loss of capture (i.e., absence of R-wave), and describes separate sensing and pacing electrodes, which are each utilized in unipolar fashion with a third common electrode having a comparatively larger dimension, to reduce residual polarization problems.

U.S. Pat. No. 3,977,411 to Hughes, Jr. et al shows a pacemaker having separate sensing and pacing electrodes which are each utilized in unipolar fashion. The sensing electrode comprises a ring electrode having a relatively large surface area (i.e., between 75 to 200 $mm^2$) for improved sensing of cardiac activity (R-waves), and is spaced along the pacing lead approximately 5 to 50 mm from the distally-located tip electrode used for pacing.

U.S. Pat. No. 3,920,024 to Bowers shows a pacemaker having a threshold tracking capability which dynamically measures the stimulation threshold by monitoring the presence or absence of an evoked response (R-wave). If no R-wave is sensed within a post-stimulus interval (e.g., 20 to 30 ms post-stimulus), the pacemaker delivers a closely-spaced backup pulse (e.g., 40 to 50 ms post-stimulus) at increased amplitude and pulse width to ensure an evoked response. Various electrode configurations are illustrated in FIGS. 1B and 9A-9F for purposes of sensing, including those of sensing with an endocardial lead extending into the right ventricle, wherein in one embodiment the sensing is between one intracardiac electrode and a reference electrode which is spaced some distance away from the heart, and in another embodiment the sensing is between intracardiac electrodes.

U.S. Pat. No. 4,305,396 to Wittkampf et al (incorporated herein by reference) also relates to a rate-adaptive pacemaker in which the output energy is automatically varied in response to the detection or non-detection of an evoked response (R-wave) and the detected stimulation threshold. For the stated purpose of facilitating prompt post-stimulus R-wave sensing, the pacemaker delivers a two-portion output, wherein the first portion comprises a positive-going recharge pulse for compensation of the repolarization caused by the stimulus pulse, and wherein the second portion comprises a negative-going stimulus pulse. Similar to the above mentioned Bowers patent, the pacemaker delivers a backup pulse within a post-stimulus interval of time (e.g., 50 to 100 ms post-stimulus) at an increased amplitude, such as twice the amplitude of the previously-delivered stimulus pulse if the applied stimulus fails to capture the heart. It is stated to be preferred to use the same electrode for both pacing and sensing, such as a unipolar or bipolar system wherein there is at least one electrode located in the ventricle, but suggests that other lead designs may be utilized such that the sensing and pacing electrode are separate.

U.S. Pat. No. 4,387,717 to Brownlee et al relates to a pacemaker having a separate (i.e., non-pacing) electrode element, implanted near or in direct contact with the cardiac tissue, and positioned relative to the pacing electrodes (i.e., unipolar pacing from "tip" to "can") to provide improved P-wave and R-wave sensing with minimal interference from the pacing electrodes. The "can" functions as an indifferent electrode for sensing in combination with the separate electrode element. The separate sensing electrode is spaced from the pacing electrodes to minimize cross coupling and interference from the pacing stimulus and after-potentials. The separate sensing electrode comprises an extravascular metallic plate having a comparatively large surface area in one embodiment. In another embodiment the separate sensing electrode comprises a cylindrical metal ring mounted on the insulated pacing lead between the pacemaker and the "tip" electrode, and is described as being located along the lead to permit positioning the sensing electrode either within the heart, externally on the heart wall, or in some remote location in the vascular system away from the heart.

U.S. Pat. No. 4,585,004 to Brownlee relates to an implantable cardiac pacemaker and monitoring system, wherein the pacing-sensing electrode system is electrically separate from an auxiliary sensing system. The auxiliary sensing system comprises a transvenous data lead with ring electrodes for sensing located in the right ventricle (approximately 1 cm from the pacing tip electrode for R-wave sensing) and in the right atrium (approximately 13 cm from the tip electrode to be in close proximity with the S-A node), both ring electrodes being used in conjunction with the pacemaker can in unipolar sensing fashion.

U.S. Pat. No. 4,686,988 to Sholder relates to a dual chamber pacemaker having atrial and ventricular endocardial leads with a separate proximal ring electrode coupled to a P-wave or R-wave sensing EGM amplifier for detecting the atrial or ventricular evoked response to atrial or ventricular stimulation pulses generated and applied to other electrodes on the endocardial lead system. The auxiliary lead system thus resembles the Brownlee '004 patent.

U.S. Pat. Nos. 4,759,366 and 4,858,610 to Callaghan, et al, incorporated herein by reference, relate to evoked response detector circuits which also employ fast recharge in at least one separate sensing electrode in either unipolar or bipolar electrode configurations in either or both the atrium and ventricle. The cardiac pacing systems function as unipolar and bipolar systems at different steps in the operating cycle. In the '610 patent, a separate electrode on the connector block of the pacemaker can is suggested for use as the reference electrode anode rather than the metal case itself if the case is employed as the reference electrode for the delivery of the stimulation pulse. In the '366 patent, the detected evoked response is used in an algorithm for adjusting the pacing rate.

U.S. Pat. No. 4,310,000 to Lindemans and U.S. Pat. Nos. 4,729,376 and 4,674,508 to DeCote, incorporated herein by reference, also disclose the use of a separate passive sensing reference electrode mounted on the pacemaker connector block or otherwise insulated from the pacemaker case in order to provide a sensing reference electrode which is not part of the stimulation reference electrode and thus does not have residual after-potentials at its surface following delivery of a stimulation pulse.

The DeCote '376 and '508 patents also set forth stimulation threshold testing algorithms for adjusting the pacing pulse energy.

Thus, considerable effort has been expended in providing electrode systems, fast recharge circuitry and separate sense amplifier systems for avoiding after-potentials and providing capture detection and stimulation threshold tracking.

Data Recording Systems—Turning to EGM data recording systems, heart rate, interval and morphology recording has been suggested in U.S. Pat. Nos. 4,003,379 and 4,146,029 to Ellinwood, Jr., and subsequently in U.S. Pat. No. 4,223,678 to Langer, et al and U.S. Pat. No. 4,295,474 to Fischell, et al. Such implantable recording systems have employed bipolar or unipolar electrode systems of the type described above in the recording of near-field or far-field EGM data. Thus the quality of EGM data recorded is limited by the limited electrode pathways and possible vectors.

Distinguishing Arrhythmias—Distinguishing malignant tachyarrhythmias from sinus tachycardias and detecting pacemaker mediated tachycardias is similarly limited by the available electrode configurations employed in single and dual chamber pacing systems, implantable drug dispensers and pacemaker-cardioverter-defibrillator systems as described above. In the context of discriminating spontaneously occurring tachyarrhythmias from sinus tachycardia, attempts have been made to employ both atrial and ventricular electrode systems in order to determine whether the tachycardia is sinus in origin or reflects a retrograde conducted abnormal ventricular rhythm. For example, it is known to have placed multiple electrodes on atrial and ventricular leads and to sense the direction of travel of a depolarization wave front as shown for example in U.S. Pat. No. 4,712,554 to Garson, Jr.

In addition, it has been found that pacemakers which operated in the DDD or related modes can, under certain circumstances, sustain a dangerous tachycardia condition particularly when operating at an upper rate limit. A pacemaker sustained or mediated tachycardia (PMT) condition is defined as an operational pacing state wherein the pacemaker erroneously stimulates the ventricle of a heart at the pacing upper rate limit for sustained periods of time. Such PMT behavior is initiated when a ventricular event occurs at a time during which the myocardial tissue between the atrium and ventricle can transmit retrograde electrical signals from the ventricle to the atrium which in turn cause an atrial depolarization. The sensing of the resulting atrial depolarization by the atrial sense amplifier in turn causes the ventricular pulse generator to emit a ventricular pacing pulse after the AV time period times out. The cycle may repeat itself if the ventricular pace event is conducted to the atrium where it again causes an atrial depolarization which is picked up by the atrial sense amplifier. This repetitive high rate stimulation may be sustained indefinitely by the pacemaker causing discomfort to the patient or possibly inducing more threatening arrhythmias.

Various techniques have been implemented to minimize th impact of PMTs, but these techniques usually sacrifice flexibility of the DDD system. U.S. Pat. No. 4,967,746 to Vandegriff sets forth a number of techniques which have been employed to alleviate PMTs.

ECG/EGM Vector Analysis—The aforementioned Lindemans U.S. Pat. No. 4,310,000 suggests various modifications to the passive sensing reference electrode depicted in its drawings, including the incorporation of more than one passive sensing reference electrode provided on or adjacent to the metallic can, positioned as deemed necessary for best sensing, and connected to one or more sense amplifiers. No specific use of the additional passive sensing reference electrodes is suggested, although the single passive sensing reference electrode is suggested for use with a sense amplifier to detect both capture and spontaneous atrial or ventricular electrical events in a dual chamber pacing system.

It is known in the art to monitor electrical activity of the human heart for diagnostic and related medical purposes. U.S. Pat. No. 4,023,565 issued to Ohlsson describes circuitry for recording EKG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems which combine surface EKG signals for artifact rejection.

The primary use for multiple electrode systems in the prior art appears to be vector cardiography from EKG signals taken from multiple chest and limb electrodes. This is a technique whereby the direction of depolarization of the heart is monitored, as well as the amplitude. U.S. Pat. No. 4,121,576 issued to Greensite discusses such a system.

In addition, U.S. Pat. No. 4,136,690 issued to Anderson, et al, shows a vector cardiographic system used for arrhythmia analysis. Similar techniques are described in "Rhythm Analysis Using Vector Cardiograms," *Transactions on Biomedical Engineering*, Vol. BME-32, No. 2, Feb. 1985, by Reddy, et al, European Pat. No. 0 086 429 issued to Sanz and U.S. Pat. No. 4,216,780 issued to Rubel, et al.

Various systems have additionally been proposed for measuring the orthogonal ventricular or atrial electrogram from multi-electrode lead systems placed endocardially within the patient's atrium and/or ventricle. Such orthogonal endocardial EGM systems are depicted in U.S. Pat. No. 4,365,639, issued to Goldreyer, and U.S. Pat. Nos. 4,630,611 and 4,754,753 issued to King. In addition, orthogonal ventricular electrogram sensing employing endocardial, multi-electrode lead systems and associated circuitry are disclosed in two articles by Goldreyer, et al, entitled "Orthogonal Electrogram Sensing," *PACE*, Vol. 6, pp. 464-469, March-April 1983, Part II, and "Orthogonal Ventricular Electrogram Sensing," *PACE*, Vol. 6, pp. 761-768, July-August 1983. In the Goldreyer patent and in these papers, it is suggested that the orthogonal electrodes be employed to detect paced events and provide capture verification as well as to facilitate the discrimination of P-waves from QRS complexes. Other articles by Goldreyer, et al., appear in the literature, including those listed in the bibliographies to these two papers.

The aforementioned King U.S. Pat. Nos. 4,630,611 and 4,754,753 describe X, Y and Z orthogonally displaced electrodes on the body of the endocardial pacing lead and circuitry for developing a composite EGM vector signal in order to detect changes in the vector over time and discriminate normal sinus rhythm from tachyarrhythmias.

Finally, U.S. patent application Ser. No. 611,901 entitled "Multi-Vector Pacing Artifact Detector," filed Nov. 9, 1990, and assigned to the assignee of the present application, sets forth a system for detecting the artificial pacing artifact in patients having artificially paced myocardial contractions in an external monitor employing three standard EKG leads with chest or limb electrodes.

Rate Adaptive Pacing—As described in the aforementioned Callaghan '610 patent, the use of physiologic parameters to develop a control signal for adapting the pacing rate to physiologic requirements has become an important aspect of current pacing systems. The stimulus-repolarization T-wave interval (Q-T interval) has been used in Vitatron ® pacemakers described in U.S. Pat. No. 4,228,803 to Rickards.

ECG/EKG Electrode Systems—numerous body surface ECG monitoring electrode systems have been employed in the past in detecting the ECG and conducting vector cardiographic studies. For example, U.S. Pat. No. 4,082,086 to Page, et al., discloses a four electrode orthogonal array which may be applied to the patient's skin both for convenience and to ensure the precise orientation of one electrode to the other. U.S. Pat. No. 3,983,867 to Case describes a vector cardiography system employing ECG electrodes disposed on the patient in normal locations and a hex axial reference system orthogonal display for displaying ECG signals of voltage versus time generated across sampled bipolar electrode pairs.

Finally, in regard to subcutaneously implanted EGM electrodes, the aforementioned Lindemans U.S. Pat. No. 4,310,000 discloses one or more reference sensing electrode positioned on the surface of the pacemaker case as described hereinbefore. U.S. Pat. No. 4,313,443 issued to Lund describes a subcutaneously implanted electrode or electrodes for use in monitoring the ECG.

SUMMARY OF THE INVENTION

In view of the aforementioned prior art, the present invention provides a method and apparatus that may be implemented into the aforementioned medical devices in order to provide an enhanced capability of detecting and gathering electrical cardiac signals via an array of relatively closely spaced subcutaneous electrodes (located on the body of an implanted device) which may be employed with suitable switching circuits, signal processors, and memory to process the electrical cardiac signals between any selected pair or pairs of the electrode array in order to provide a leadless, orientation insensitive means for receiving the electrical signal from the heart.

This sensed far-field EGM may be used to provide storage and analysis of arrhythmic events and to provide control signals for the delivery of various therapies including pacing, cardioversion and defibrillation therapies as well as the delivery of antiarrhythmic drugs, and, in the pacing context, to effect capture detection and automatic stimulation threshold adaptation, recording of PMT episodes, measurement of refractory periods in order to set timing windows for antitachycardia pacing therapies, and as a control signal for use in adjusting pacing rate to physiologic demand.

The housing or case of the subcutaneously implanted medical device is modified to provide an array of electrodes which may be selectively or sequentially coupled in one or more pairs to the terminals of one or more sense amplifiers to pick up, amplify and process the electrical cardiac signals across each electrode pair. In one embodiment, the signals from the selected electrode pairs may be stored and compared to one another in order to determine the sensing vector which provides the largest cardiac signal (in a test mode). Following completion of the test mode, the system may employ the selected subcutaneous ECG signal vector for a number of applications.

The implanted device possesses analog-to-digital conversion circuitry for sampling and converting the selected subcutaneous ECG signal to digital data which is stored in a recirculating buffer, the contents of which are transferred to RAM for later data retrieval either periodically or upon the occurrence of an event of interest. In another embodiment, the selected subcutaneous ECG signal is used to confirm capture in conjunction with an algorithm for determining the stimulation threshold of the heart and set stimulation pulse energy at a level exceeding the threshold by a desired safety margin.

Further embodiments include replacing the switching approach with parallel linear and nonlinear combinational processing of the signals from the orthogonal electrode pairs of the electrode array, to develop and employ continuous signals insensitive to the orientation variations of the electrode array. These linear and nonlinear embodiments would be used for improving the data storage and autocapture embodiments by providing an optimal signal at all times, while avoiding the switching process.

In the context of a DDD pacing system, the EGM signals from selected pairs of electrodes may be stored in RAM during periods of time when sustained upper rate limit pacing is occurring in order to provide a diagnostic record for analysis by the physician upon readout of the RAM contents by uplink telemetry under the control of an external programmer. In addition, it may be possible to employ characteristics of the far-field EGM signal generated during PMT behavior to detect subsequent PMT episodes and initiate appropriate response thereto.

In the context of any of the above devices, and including drug administration devices and tachyarrhythmia control devices, a patient may be provided with a limited function external controller to initiate storage of or transfer of such far-field EGM signals into RAM when the patient experiences the onset or recovery from an arrhythmia such as syncopy and atrial or ventricular tachycardias.

These and other objects and advantages of the present invention may be realized in a method and apparatus for providing at least first, second and third electrodes spatially oriented on the periphery of the device case or in close proximity thereto in a preset array.

BRIEF DESCRIPTION OF THE DRAWINGS

The present invention will be better understood, and its attendant advantages will be readily appreciated, by reference to the accompanying drawings when taken in consideration with the following detailed description, wherein:

FIGS. 4A-4C are representations of the received signals and vector magnitudes of the three different principal far-field EGM cardiac vectors of FIGS. 3A-3C as reflected on the X and Y axes of the three electrode array;

DETAILED DESCRIPTION OF THE PREFERRED EMBODIMENTS

The Subcutaneous ECG (Far-Field EGM) Electrode Array—As set forth above, the present invention contemplates the provision of an array of electrodes situated on or in proximity to an implanted medical device outside the patient's heart coupled with logic means and interconnecting circuitry for selectively detecting signals representative of the far-field EGM detected across selected combinations of the electrodes and the processing of such information to record the selective electrograms in storage for subsequent read-out on the occurrence of certain events and the development of control signals for controlling or modifying the operation of the medical device in accordance with specific attributes of the processed far-field EGM signal. The following specific preferred embodiments are intended to be illustrative of applications of this concept without limiting the scope of the invention as claimed.

Figure 1:
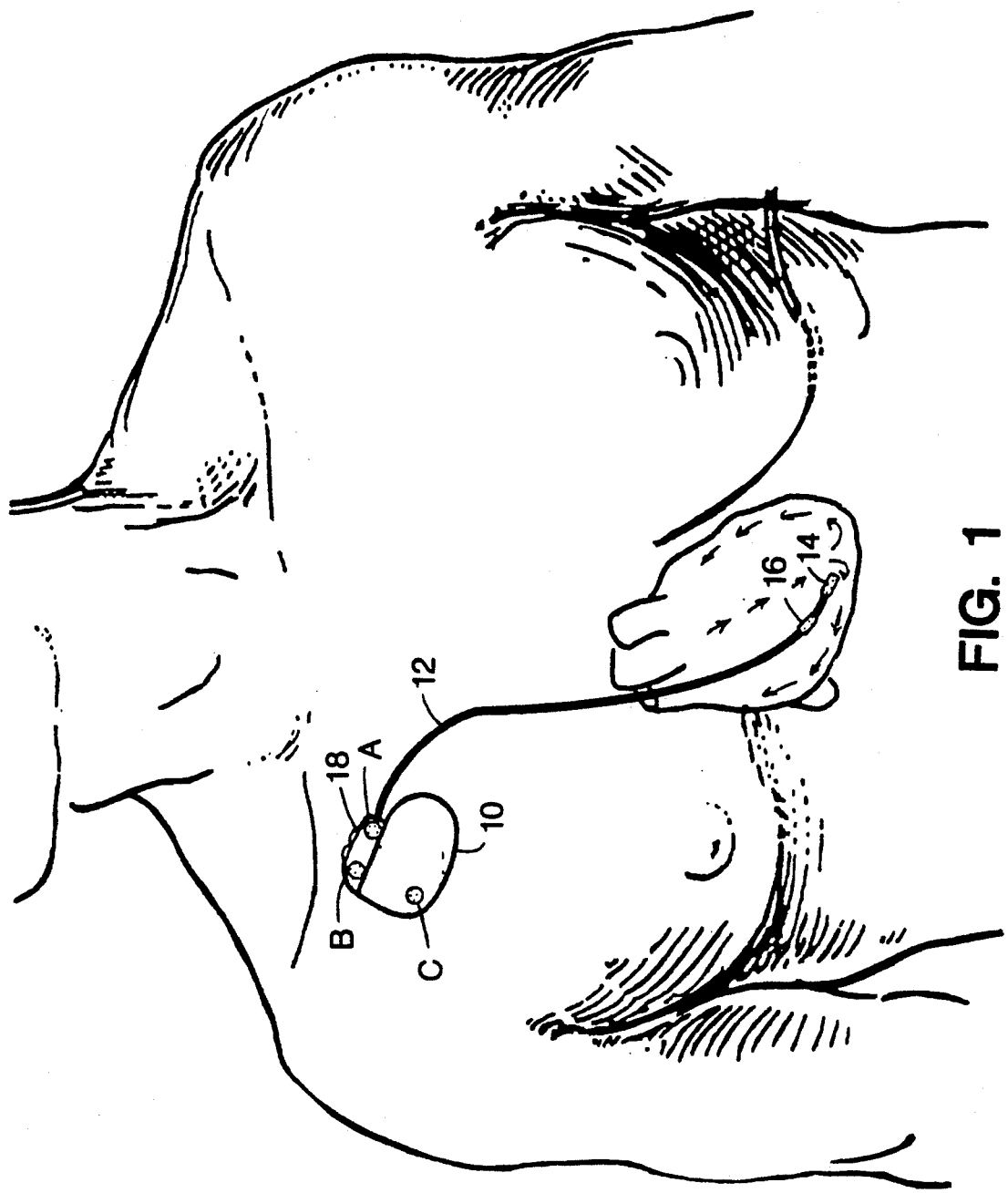
FIG. 1 is an illustration of the placement of a pacemaker pulse generator and lead system in accordance with the present invention and the directional vectors of the depolarization wavefront of cardiac tissue.

Turning now to FIG. 1, an implanted medical device, in this case a multi-programmable ventricular demand pacemaker is depicted in order to show the orientation of the array of electrodes A, B, and C in relation to the pacemaker pulse generator housing 10, the endocardial lead 12, the distal tip and ring electrodes 14 and 16, respectively, residing within the right ventricle of the patient's heart and the connector block 18 of the pulse generator. An array of three electrodes A, B, and C disposed orthogonally on the surface of the pulse generator 10 and connector block 18 and facing outwardly towards the patient's skin is employed to develop the far-field EGM signal comprising the PQRST signals generated in the sequential depolarization of the atrium and ventricle of the patient's heart.

Although the expression "far-field" is normally employed for sensing between a relatively wide spaced electrode (usually disposed within a chamber of the patient's heart) and a remote electrode or the sensing of a P-wave in the ventricle or an R-wave in the atrium, for purposes of this invention, the expression relates to the EGM picked up between these relatively closely spaced electrodes in the illustrated electrode arrays, wherein the array itself is remote from the heart. Due to the positioning of the array, the signals may also be referred to as "subcutaneous ECG" signals.

Although not specifically depicted in FIG. 1, it will be understood that the medical device may constitute a pacemaker-cardioverter-defibrillator arrhythmia control device having additional cardioversion/defibrillation electrodes disposed in and about the patient's heart as shown, for example, in U.S. Pat. No. 4,727,877 issued to Kallok et al, as well as in U.S. patent application Ser. Nos. 612,758; 612,760; and 612,761, all filed Nov. 14, 1990, in the names of Keimel or Keimel, et al, all assigned to the assignee of the present application and incorporated herein by reference. Alternatively, the electrodes A, B, C may be disposed on the surface of the multi-programmable, microprocessor driven automatic drug administration device of the type set forth in the aforementioned Ellinwood patents incorporated herein by reference.

In all such systems, it will be understood that the electrodes A, B, C are electrically isolated from one another and the conductive surface of the pulse generator housing 10 through suitable insulating bands and electrical feedthroughs as described in the aforementioned Lindemans U.S. Pat. No. 4,310,000, incorporated herein by reference. Examples of possible electrode orientations and configurations of a three electrode system comprising electrodes A, B and C are set forth in FIGS. 2A to 2E.

Figure 2A:
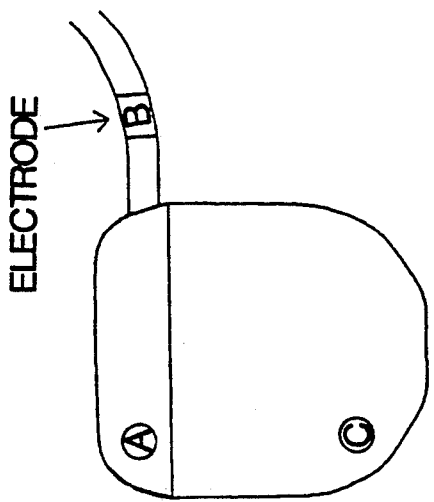
FIGS. 2A-2E are schematic illustrations of possible three electrode positions on the case and/or lead of an implantable medical device for practicing the concepts of the present invention.

Turning to FIG. 2A, it illustrates the orientation of orthogonally disposed electrodes A, B and C with two electrodes on the connector block 18 and one electrode on the pulse generator case 10. The spacing of the electrodes A, B and C on each of the illustrated orientations of FIGS. 2A to 2E as well as in FIG. 1 is on the order of about one inch but can be larger or smaller depending on the exact size of the device. Smaller devices and closer spacing will require greater amplification.

Figure 2B:
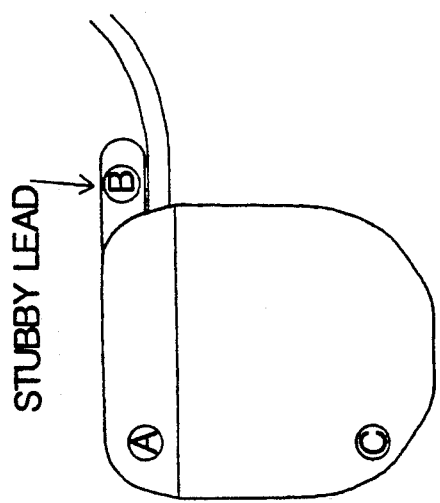
Figure 2C:
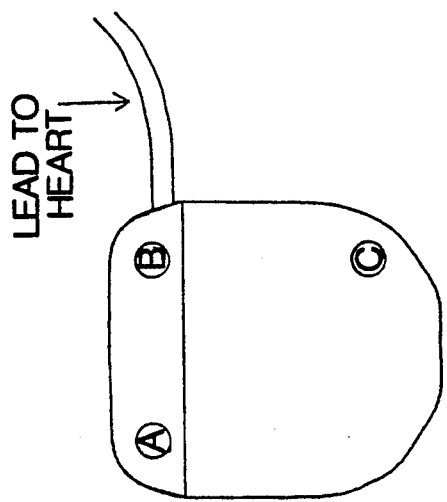

Turning now to FIGS. 2B and 2C, the size of implantable pulse generators, particularly single chamber cardiac pacemakers, is growing progressively smaller. FIGS. 2B and 2C illustrate locations of at least one of the electrodes extended away from the pulse generator by a stubby lead extension 20 in FIG. 2B and a segment of the lead itself in FIG. 2C in order to achieve a greater inter-electrode spacing, if desirable.

Figure 2D:
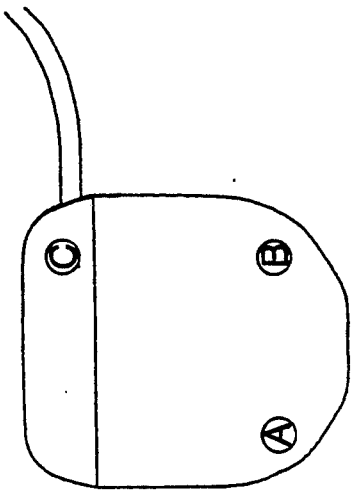
Figure 2E:
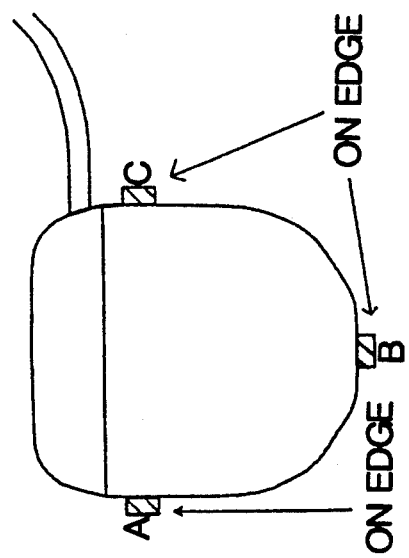

As illustrated in FIGS. 2C and 2D, the relative orientation of the electrodes may vary somewhat from the orthogonal orientation depicted in FIGS. 2A and 2B. Although orthogonal electrode orientations are preferred, it will be understood that other angular orientations will suffice and perhaps even be preferred depending on the number of electrodes employed and the signal processing capability of the implanted device.

FIG. 2D depicts the electrodes A, B and C along the sides of the pulse generator 10.

It will be understood that the electrodes placed on the edge of the pulse generator case depicted in FIG. 2D could constitute insulated pins of feedthroughs extending through the wall of the case.

The far-field EGM reflecting the amplitude and rate of change of the PQRST complex may be sensed throughout the body tissue as an electric field emanating from the electrical depolarization of the heart muscle depicted in FIG. 1. As the cardiac muscle depolarizes, the direction of the depolarizing wave front changes as the atrium initially depolarizes and then the ventricle depolarizes down the intraventricular septum to the apex of the heart where the direction of the depolarization changes as the wave front travels back up towards the pacemaker through the ventricular muscle mass. Consequently, the far-field EGM sensed across the three electrodes A, B, C disposed on the case when usually (but not necessarily) situated pectorally will be observed to change both in amplitude and polarity depending on the orientation of the measuring pair of electrodes to the electric field orientation of the electrical depolarization wave front.

The electrodes A, B and C are fixed in position unless the pulse generator is either moved by the patient or becomes loose in the pocket. In any case, for most applications, it is desirable to optimize the sensing of the peak amplitude of the R-wave for applications relating to simple rate calculation, capture detection or the like by selecting the electrode orientation that provides the highest amplitude R-wave output signal. For other applications, as explained hereinafter, where it is desirable to obtain faithful reproduction of both the amplitude and slew rate of sampled points of the QRS complex, more elaborate signal processing schemes are described.

Figure 3A:
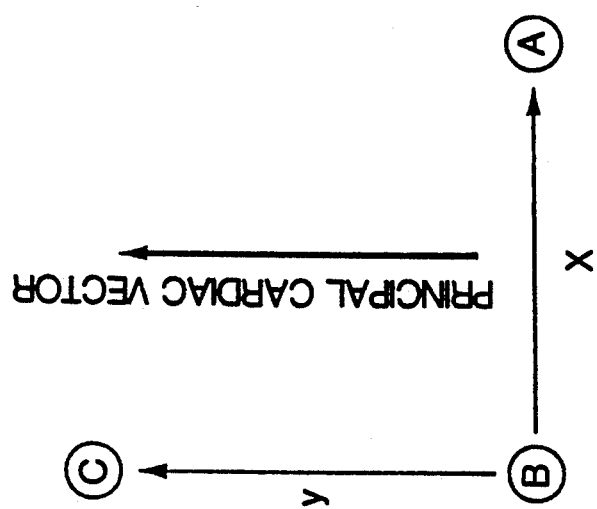
FIGS. 3A-3C are representations of three principal cardiac vector orientations with reference to the X and Y axes in a three electrode orthogonal array.
Figure 3B:
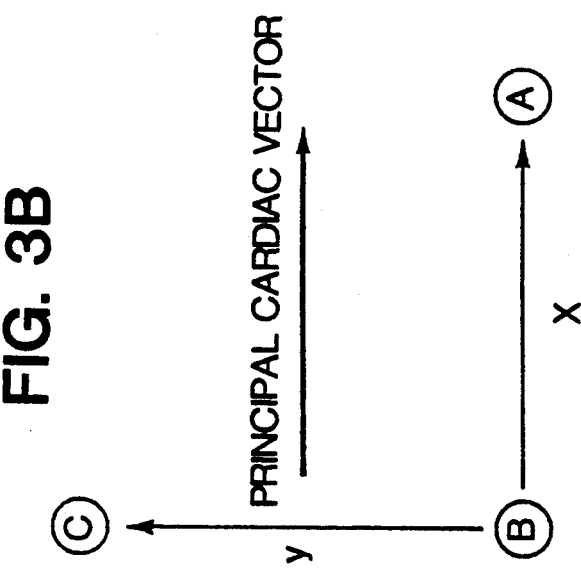
Figure 3C:
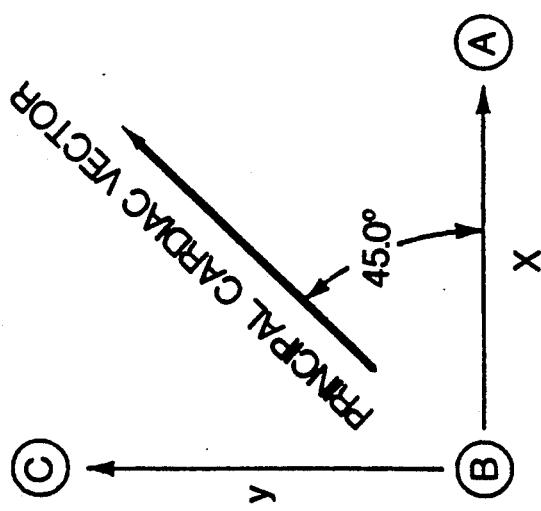

Assuming that the electrode positions are fixed, FIGS. 3A to 3C depict possible far-field EGM vectors seen at the electrodes A, B and C. For ease of illustration, the vector is shown passing through the electrode B in relation to the X and Y directions defined by the straight line paths between electrodes C-B and A-B, respectively. It will be understood that the vectors depicted in FIGS. 3A to 3C represent the orientations of the cardiac vector for the R-wave peak which is depicted in the top line of the "vector EGM" line of FIGS. 4A to 4C. In this example of FIGS. 3A to 3C and 4A to 4C, it will be assumed that the three vector EGMs are identical and possess the identical vector direction but that the electrodes A, B and C are rotated in position with respect to that fixed vector. Incidentally, FIGS. 3A to 3C can also illustrate the change in direction that the vector itself may make depending on the instantaneous orientation of the depolarization wave format in the heart muscle. For ease of illustration, it will be assumed that the vectors of FIGS. 3A to 3C possess the same polarity and reflect the vector associated with the peak amplitude as shown in the vector EGM depiction of FIGS. 4A to 4C.

Figure 4B:
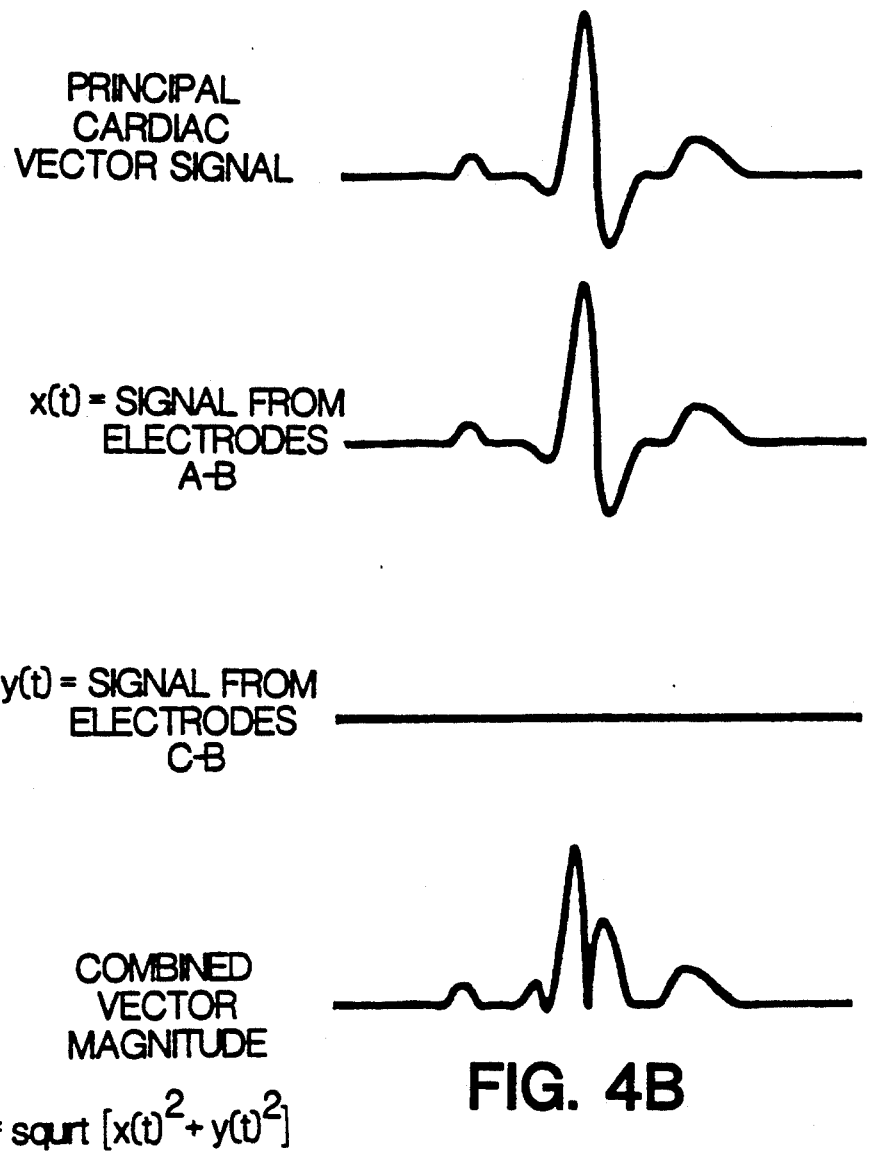
Figure 4C:
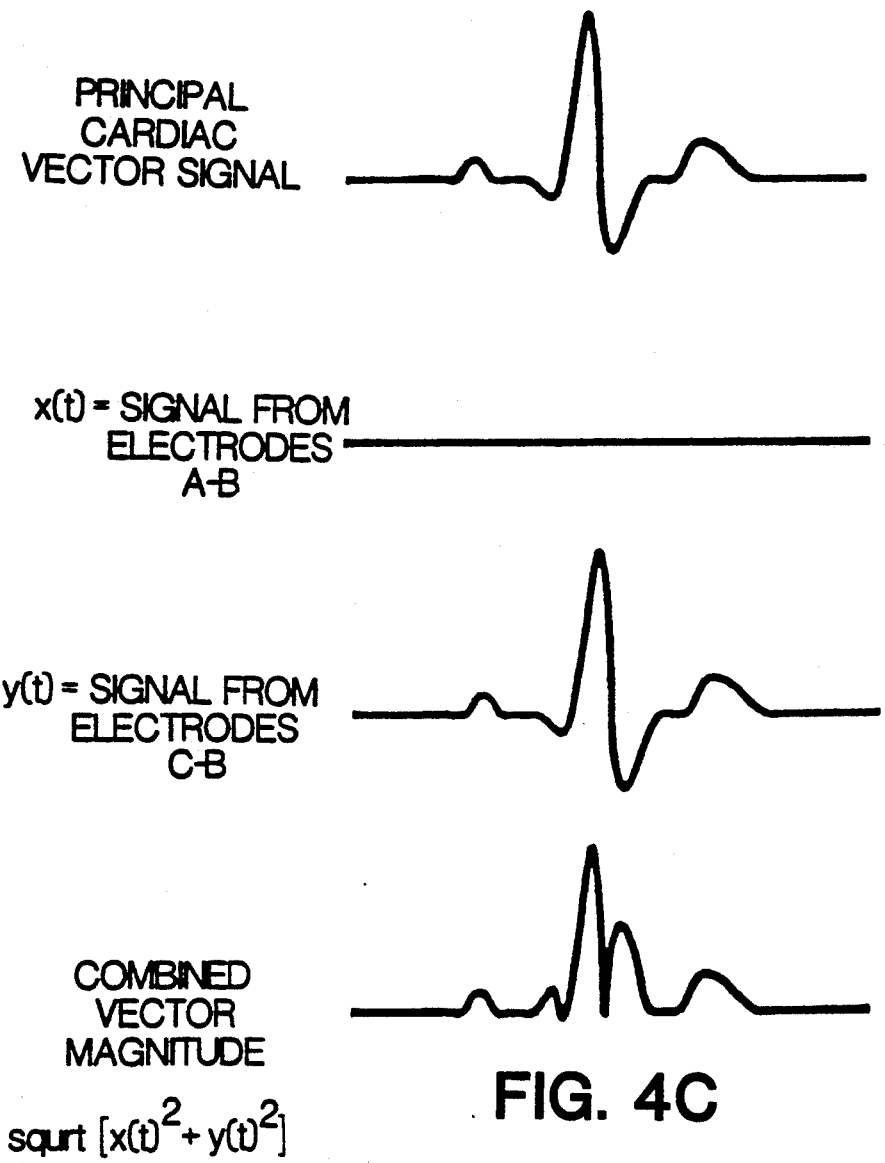

FIGS. 4A to 4C depict the projection of the amplitude of the vector EGM depicted in the top line of each drawing onto the Y and X directions defined by the path between the electrodes A-B and C-B and the mathematical processing that may be undertaken to determine the vector magnitude from the magnitude of the signals on the abscissa and ordinate regardless of the direction of the vector. As shown in the fourth line of FIGS. 4A to 4C, the magnitude reflects the vector EGM magnitude depicted in the top line with square root of sum of squares conversion of the signal.

In FIG. 3B, the vector representing the orientation of the maximum far-field signal from polarizing wave front is perpendicular to the path C-B and consequently cannot be sensed across that electrode pair. The full magnitude of the principal cardiac vector EGM may instead be sensed across the electrodes A-B. Similarly, in FIG. 3C, the vector is in the direction of the path C-B and the full magnitude of the principal cardiac vector may be sensed by a sense amplifier coupled across electrodes C and B.

Turning to FIG. 3A, for convenience, the vector is shown oriented at 45° degrees to the abscissa and ordinate and consequently the amplitude of the far-field EGM that would be sensed across the electrodes A-B and C-B is approximately 71 percent of the principal cardiac vector. Thus the combined signal processed from the two signals across electrodes A-B and C-B is identical to the combined vector magnitude signals depicted in FIGS. 4B and 4C indicating orientation independence.

The availability of a fixed orthogonal array on a substrate that remains fixed in position at a location outside the patient's heart advantageously is employed in the present invention in a variety of device contexts. Different receiving orientations may be developed mathematically or mechanically from the electrogram signals developed in the directions A-B and C-B so that a set of far-field EGMs may be developed in a full 360° array of received orientations. For most purposes, the three electrode array in a single plane depicted in FIGS. 3A-3D is sufficient to provide meaningful far-field EGM recordings and control signals.

The selective and sequential coupling of the electrode pairs illustrated in FIGS. 3A-3C may be tailored to develop desired far-field EGM data for recording the data for subsequent read out and analysis and/or for developing control signals affecting the operation of the implanted device in many ways. In the context of capture detection, it is contemplated that after the delivery of a stimulating impulse across the electrodes 14 and 16 depicted in FIG. 1, the EGM may be measured between a first electrode pair, such as pair C-B, absolute valued, peak or slope value detected, converted from analog to digital data and stored in a buffer. Subsequently, EGMs may be received between the other electrode pair and likewise processed and stored in memory within the implanted device. After both signals are stored in buffers, they may be compared and the signal having the greatest amplitude and also exceeding a preset threshold amplitude may be identified. Subsequently, the electrode pair which develops the identified highest amplitude far-field EGM signal may be employed for periodically verifying capture.

Going a step further, and to avoid the use of the switching circuitry, it is possible to mathematically combine the EGM signal sensed across the electrodes A-B and C-B in a nonlinear combining circuit network which provides a signal that represents a summation of the signals sensed across the two electrode pairs in the manner depicted as the combined vector magnitude signal in FIGS. 4A-4C.

It should be kept in mind that the signals from the closely spaced orthogonal pairs of far-field electrodes can be considered together to represent a dynamic (time-varying) vector-electrogram which together describe the dynamically changing local far-field electric field vector at their centerpoint. This can be considered to be a realistic measure of the local electric field vector since the electric field is nearly locally uniform since the electrodes are closely spaced compared to the distance to the source of the electric field variations—the depolarized heart.

Thus the pair of orthogonally measured signals X(t) and Y(t) between A-B and C-B comprise a time varying vector: $\bar{z}(t) = \hat{x}(t)x + \hat{y}(t)y$ where $\hat{x}$ and $\hat{y}$ represent unit vectors corresponding to the orthogonal axis of the three electrodes. The vector magnitude and phrase (orientation angle) of $\bar{z}(t)$ can be calculated per standard vector mathematics as:

$$\text{Vector Magnitude } (\bar{z}(t)) = \sqrt{x(t)^2 + y(t)^2}$$

$$\text{Phase Angle } (\bar{z}(t)) = \arctan\frac{(y(t))}{(x(t))}$$

by determining the vector magnitude of $\bar{z}(t)$, an orientation insensitive signal can be produced which can be used advantageously to overcome rotational variations.

In addition the vector orientation which produces the maximum vector magnitude of $\bar{z}(t)$ corresponds to the principal cardiac vector discussed in the cardiovascular literature. An electrode axis orientation in line with the principal cardiac vector will produce a far-field electrogram signal with the maximum peak amplitude as shown in FIGS. 3B and 3C. However, it is not necessary to physically reorient the electrode axis to retrieve this signal when one employs a pair of orthogonal electrodes. It is merely necessary to mathematically recreate the signal that would be received if one of the pairs of electrodes were rotated to align with the principal cardiac vector orientation. This can be done per FIG. 12A to be described hereinafter.

EGM Signal Recording and Storage—Turning to signal recording and storage, it may be seen that the aforementioned signals may be selected for either sequential or simultaneous recording of the EGM data depending on the available signal processing channels and storage and telemetry capacity of the implanted medical device. However, in the interest of obtaining high resolution and faithfully reproduced representations of the far-field EGM, it is desirable to employ at least the nonlinear combining circuitry described above or preferably to employ a linear combining circuit network with signal axis rotation. Each of these signal processing circuits will be described hereinafter in conjunction with the description of the preferred system embodiments of the invention.

The events initiating automatic recording of data may include the operation of a dual chamber cardiac pacemaker at its upper rate limit for a sustained number of beats or predetermined period of time, the switching of the pacing mode from an atrial synchronous mode to a rate responsive mode in response to elevated atrial rates, to track the underlying behavior of the heart in a PMT or spontaneous atrial tachycardia, the detection of an arrhythmia in a tachyarrhythmia control device, the delivery of arrhythmia breaking therapies, and the response of the heart to the delivery of a bollus of medication in an automatic drug administration device. Alternatively, a purely diagnostic system may be implanted in order to record the patient's far-field EGM in patient's suffering from recurrent bouts of syncopy which defy diagnosis by external monitoring and control by drug therapies. The remaining Figures depict signal processing circuitry on systems for implementing the concepts of the invention into preferred embodiments thereof.

Figure 5:
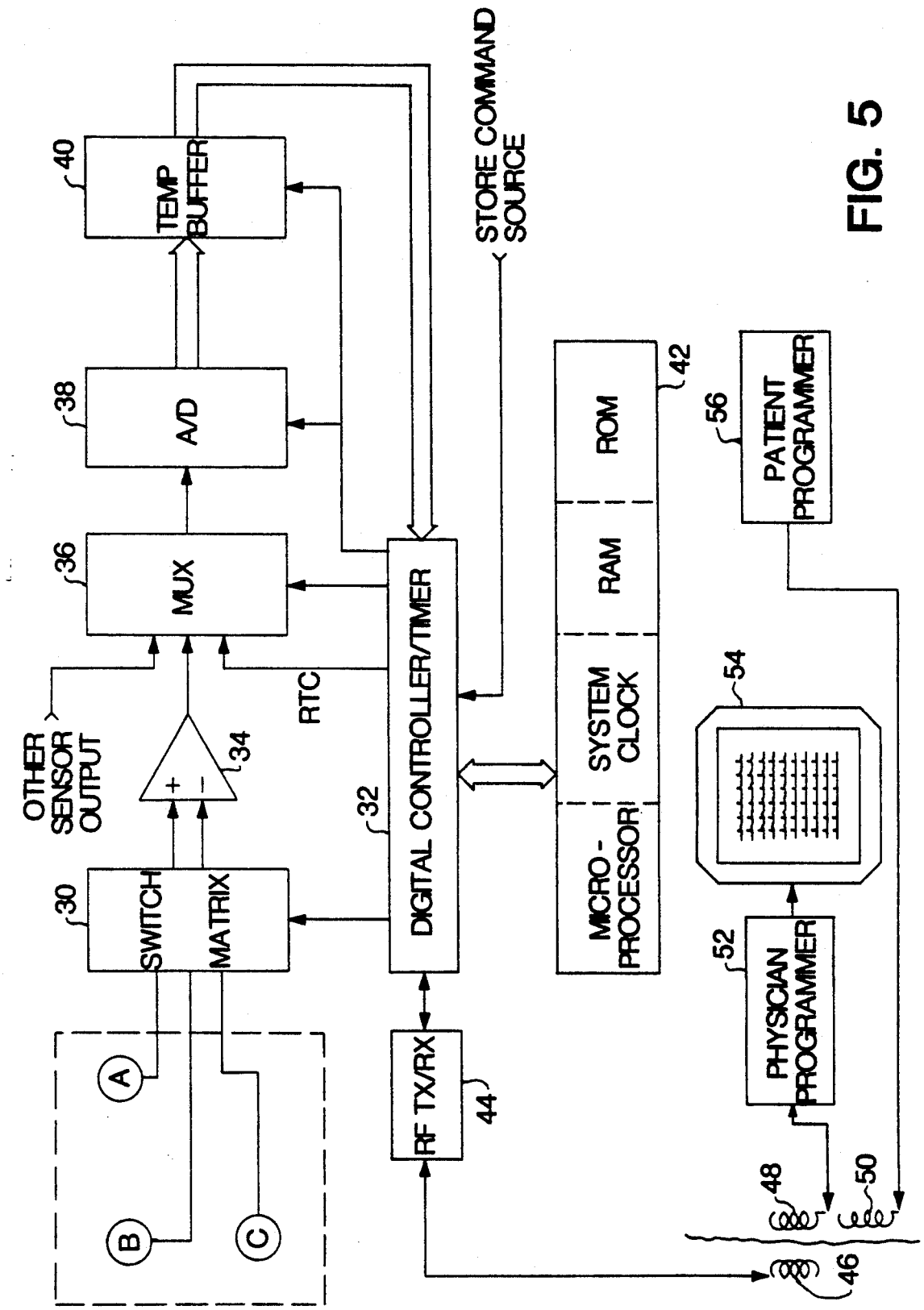
FIG. 5 is a simplified block diagram of an implantable medical device for detecting and storing far-field EGMs between one or more pairs of electrodes of the electrode arrays depicted in the preceding drawings in conjunction with alternate signal processing circuits of the following drawings and external programmers for initiating storage, read out and/or display of such stored EGMs.

Turning now to FIG. 5, a recording system for initiating the storage of selected far-field EGM data into RAM upon a STORE command from one of the aforementioned sources as well as commands telemetered in by a physician employing a physician programmer or a patient employing a limited function patient programmer is depicted. In FIG. 5, the electrodes A, B and C are coupled to the switch matrix 30 which operates under the control of the digital controller/timer block 32 to switch the EGM signal developed across at least one electrode pair A-B or C-B through amplifier 34 to one input of multiplexer 36 which also operates under commands delivered by digital controller/timer 32 to direct the EGM signal or a sensor output signal or a real time clock time tag to A/D converter 38 which operates to sample the time varying analog EGM signal and digitize the sampled points in the well known fashion. The digital output of the A/D converter 38 is applied to a temporary buffer 40 which shifts the digital data through its stages in a FIFO manner under the control of the digital controller/timer 32. The temporary buffer 40 may have a capacity of 20 to 30 seconds of continuous digitized EGM data although longer periods are contemplated in certain situations described hereafter.

The data stored in temporary buffer 40 is transferred into RAM in the microcomputer block circuit 42 when a STORE command is received from a STORE command source or when a programmed in store command signal is received through the radio frequency transmitter/receiver circuit block 44. As is well understood, the radio frequency transmitter/receiver block 44 receives other commands to program the operation of the implantable device or to readout its state or mode of operation and operating parameters as well as stored data of the type contemplated to be stored in the present invention.

The radio frequency transmitter/receiver circuit block 44 is connected to an implanted radio frequency antenna 46 which may be RF coupled to an external antenna 48 or 50 in a manner well known in the prior art. Two external command programming systems are contemplated, the first, a physician programmer and display 52 and 54 connected to transmitter/receiver antenna 48, and a second, limited function, patient programmer 56 coupled to transmitter/receiver antenna 50.

FIG. 5 depicts the memory storage functions of the present invention in a general fashion which may be implemented in any of the devices previously described. The STORE command source for a cardiac pacemaker may be the instruction to store upon the delivery of a pacing pulse, the data related to the capture or noncapture of the patient's heart, the operation at the upper rate limit or the detection of high atrial rates as mentioned hereinbefore. In conjunction with rate responsive pacemakers, the STORE command may also precipitate storage of digitized sensor output signals.

In the context of an arrhythmia control device, such as a pacemaker-cardioverter-defibrillator, the STORE command may precipitate storage of the electrogram preceding and following detection and delivery of a therapy. In the context of a drug administration device, the STORE command may precipitate the storage of data related to the detection of an arrhythmia or an abnormal cardiac function detected by another sensor and the delivery of a bollus of medication.

The external physician programmer 52 may be employed by the physician in working up the patient in the course of a drug or electrophysiologic study. In such circumstances, the programmer software may be designed to instruct the digital controller/timer 32 and the microprocessor within block 42 to direct the output of the A/D converter 38 directly to the RF transmitter/receiver block 44 in real time for telemetry out, reception by the programmer 52 and display on the display panel 54. Alternatively, the physician programmer 52 may be employed to read out the contents of the RAM devoted to the storage of the digitized EGM, sensor, and time tag data for display and recording.

In a certain segment of patients suffering recurring bouts of syncopy, the system of FIG. 5 (simplified by substitution of digital logic for the microprocessor within block 42) could be implanted with or without rate detection circuitry for detecting syncopy and automatically triggering the storage of data. Alternatively, it is contemplated that a limited function patient programmer 56 and transmitting antenna 50 be provided for use by the patient upon recovery from a bout of syncopy. When a patient experiences syncopy lasting more than a few seconds, they typically faint and recover a short time thereafter. The storage of several minutes of EGM prior to and during the syncoptal episode and for a time thereafter would constitute valuable data in the analysis of the rhythm disturbance precipitating the episode.

Such a system would include a 512 byte direct memory accessed buffer 40. Under internal ROM software direction, the digital controller/times and microcomputer 42 directs acquisition of data into buffer 40 and transfer of that data into one or two dedicated storage registers in RAM. At a sampling frequency of 128 or 256 Hz, one long (15.8 minutes) or two short (7.9 minutes each) episodes may be stored in a 32K byte static RAM, with data compression.

When the buffer 40 fills, the data compression algorithm executes. Every other point is initially discarded if the sample rate of 128 is selected. Two passes of turning point data compression, followed by a data dependent compression algorithm similar to run length coding, results in an approximate 4:1 data reduction. After data compression, 32 or 64 bytes of storage in permanent memory results, if an initial sample rate of 128 or 256 Hz is selected, respectively.

The preferred system involves patient initiation of A/D data collection in one of two modes. In mode one, the subcutaneous ECG is continuously recorded 40 at 256 samples per second, transferred via DMA to buffer 40. Every other point is then discarded if the data compression sample rate of 128 is selected. The data is then compressed by a factor of 4:1 via two consecutive 2:1 turning point algorithms, and then stored in the 32K byte RAM of data storage memory. If FREEZE mode is selected, application of a magnet and subsequent reed switch closure causes the data stored in RAM to be frozen, and A/D EGM data collection to cease after a programmed period of time. The stored data is transmitted out through the RF link upon application of a magnet and receipt of an interrogation command transmitted in by programmer 52. In FREEZE mode two, the initial application of the magnet freezes data in one half of the available RAM memory. Data collection will continue utilizing the second half of RAM storage memory. A second application of the magnet freezes the new data in the remaining RAM storage memory. In this way two segments of EKG may be stored by the patient. Uplink of the data occurs in the same manner as mode one.

In ROLLING mode, application of the magnet triggers the freezing of data continuously being loaded in half the storage memory. As in the FREEZE mode, data continues to be gathered post-trigger for a programmed period of time. The data loading then continues in the other half of the storage memory. In subsequent applications of the magnet, the data acquisition switches between freezing data storage in one buffer and loading data in the other. In this way the FREEZE mode stores the earliest one or two patient activated events while the ROLLING mode always stores the last patient activated data storage event.

The physician may use the programmer 52 to initiate real time transmission out of the EGM for external storage and display by keying in the REAL TIME ECG TRANSMISSION command which causes continuous transmission out of the subcutaneous EGM at 512 Hz. Storage of data in memory and data compression does not occur while real time data is being transmitted. Removal of the programming magnet or keying in the CANCEL REAL-TIME ECG TRANSMISSION command terminates the transmission of real time EGM.

In a simplified system, it is contemplated that the patient programmer 56 and antenna 50 may be eliminated in favor of a magnetically actuable reed switch implanted in the device and coupled to the digital controller/timer 32 that may be closed by the patient placing a magnet over the implanted device as well known in the prior art. It is further contemplated that the real time clock be incorporated within all of the above mentioned systems in order to provide a time tag with the stored data to determined whether or not episodes are circadian.

The telemetry out of the EGM data and other sensor data is preferably implemented employing pulse position modulation techniques described in co-pending U.S. patent application Ser. No. 468,407 filed Jan. 22, 1990 in the names of Wyborny et al, assigned to the assignee of the present application and incorporated herein by reference. Such high rate transmission techniques facilitate the telemetry out of time varying digitized EGM data.

The selection of the electrode pairs A-B or C-B in FIG. 5 may be accomplished by the switching matrix 30 either automatically in a fashion to be described hereinafter or by suitable transmitted in selection commands initiated by the physician. In the course of testing the system after implantation, the physician may employ the programmer 52 to select the electrode pairs A-B, C-B or even C-A and observe the telemetered far-field signals on display 54. Upon observing the relative amplitudes of the EGM signals, the physician may program in the selected pair for subsequent clinical use by the patient.

Alternatively, and preferably, the far-field EGM signal sensed across the electrode pairs A-B and C-B may be combined electronically to provide the combined vector magnitude signal depicted in FIGS. 4A–4C from the far-field vector EGM signal deflected across the electrode pairs A-B and C-B as described hereinbefore. The particular circuitry for automatically selecting the highest amplitude electrode pair is described hereinafter in conjunction with FIGS. 7 and 8. The parallel processing of the far-field EGM signals sensed across the electrode pairs A-B and C-B with alternate nonlinear and linear combination approaches are described in conjunction with FIGS. 10, 11A–11C and 12A–12C hereinafter.

Figure 6:
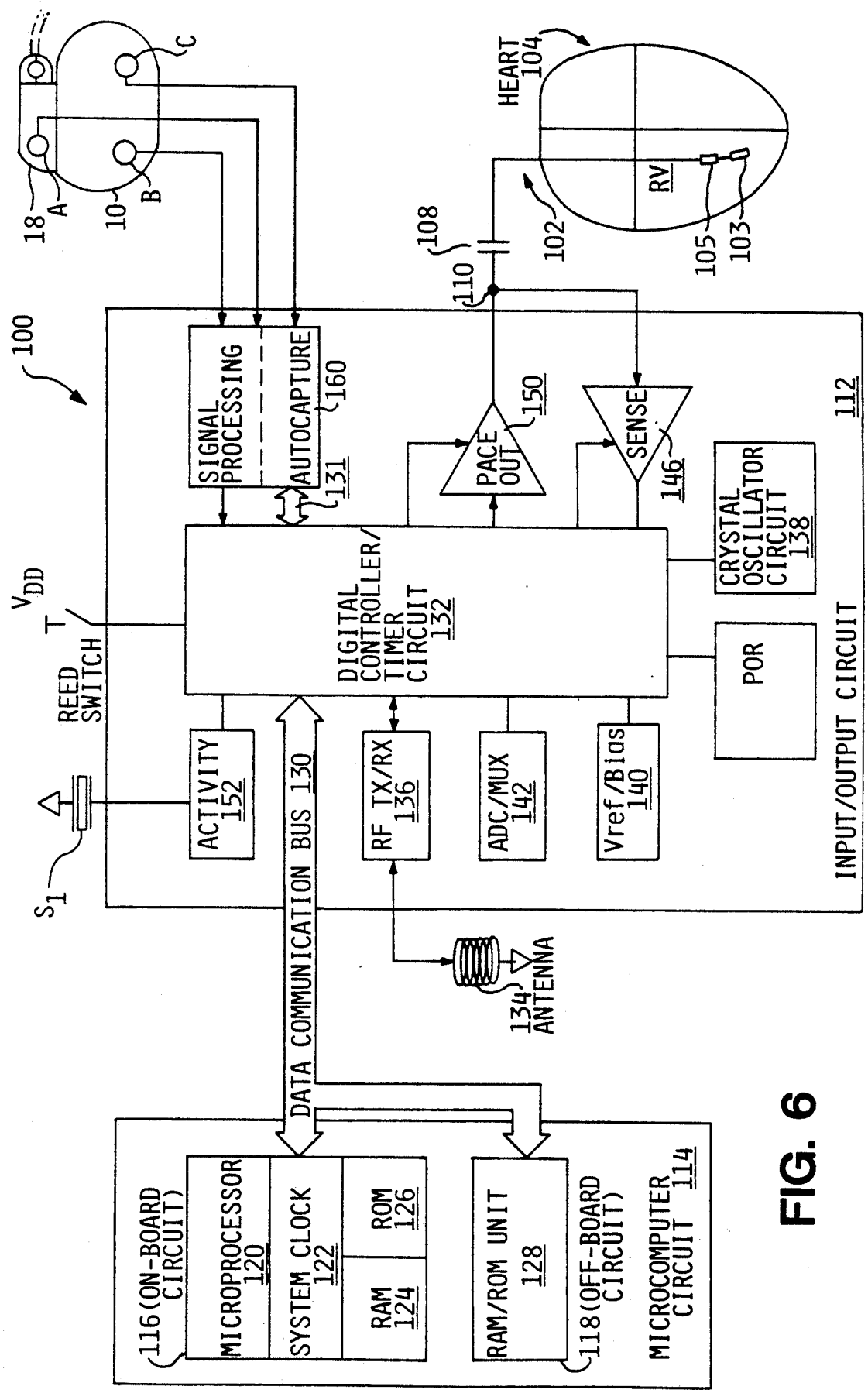
FIG. 6 is a simplified block diagram of a pacing system within which the far-field EGM detection and storage system of FIG. 5 and the alternate signal processing and capture detection of the following drawings may be incorporated.

Turning now to FIG. 6, it depicts a block circuit diagram illustrating a bradycardia pacemaker incorporating the concepts of the present invention. In the preferred embodiment of FIG. 6, the pacemaker circuit 100 is schematically shown electrically coupled via a pacing lead 102 to a patient's heart 104. Lead 102 includes bipolar electrodes 103 and 105 at the distal end of lead 102 and positioned within the right ventricle (RV) of the patient's heart 104. Lead 102 can carry either unipolar or bipolar electrodes as is well known in the art. In the preferred embodiment, the lead 102 which couples pacemaker to the ventricular endocardium comprises a steroid-tipped electrode, bipolar lead. Electrodes 103 and 105 are coupled via suitable lead conductors through output capacitor 108 to node 110 and to input/output terminals of an input/output circuit block 112.

The input/output circuit 112 contains the operating input and output analog circuits for digital controlling and timing circuit 132 necessary for the detection of electrical signals derived from the heart, such as the R-wave and the far-field EGM, as well as for the application of stimulating pulses to the heart to control its rate under the control of software-implemented algorithms in a microcomputer circuit 114 and control and data signals traversing data buses 130 and 131.

Microcomputer circuit 114 comprises an on-board circuit 116 and an off-board circuit 118. On-board circuit 116 includes a microprocessor 120, a system clock 122, and on-board RAM 124 and ROM 126. Off-board circuit 118 includes an off-board RAM/ROM Unit 128. Microcomputer circuit 114 is coupled by data communication bus 130 to a digital controller/timer circuit shown at 132. Microcomputer circuit 114 may be fabricated of custom IC devices augmented by standard RAM/ROM components. It will be understood that the electrical components represented in FIG. 6 are powered by an appropriate implantable-grade battery power source (not shown).

An antenna 134 is connected to input/output circuit 112 for purposes of uplink/downlink telemetry through an RF transmitter/receiver circuit (RF TX/RX) shown at 136. Telemetering both analog and digital data between antenna 134 and an external device, such as an external programmer (not shown), is accomplished in the preferred embodiment by means of all data first being digitally encoded and then pulse position modulated on a damped RF carrier, as substantially described in the aforementioned co-pending U.S. patent application Ser. No. 468,407.

A crystal oscillator circuit 138, typically a 32,768 Hz crystal-controlled oscillator, provides main timing clock signals to digital controller/timer circuit 132. A Vref/bias circuit 140 generates a stable voltage reference and bias currents for the analog circuits of input-/output circuit 112. An ADC/multiplexer circuit (ADC/MUX) 142 digitizes analog signals and voltages to provide telemetry and replacement time indicating function (EOL). A power-on-reset circuit (POR) 144 functions as a means to reset circuit and related functions to a default condition upon detection of a low battery condition, which will occur upon initial device power-up or transiently occur in the presence of electromagnetic interference, for example.

The operating commands for controlling the timing of the pacemaker depicted in FIG. 6 are coupled by bus 130 to digital controller/timer circuit 132 wherein digital timers set the overall escape interval of the pacemaker, as well as various refractory, blanking and other timing windows for controlling the operation of the peripheral components within input/output circuit 132.

Digital controller/timer circuit 132 is coupled to a sense amplifier (SENSE) 146 for receiving amplified and processed signals picked up from electrodes 103, 105 through lead 102 and capacitor 108 representative of the near-field electrical activity of the patient's heart 104. SENSE amplifier 146 produces a sense event signal for re-setting the escape interval timer within circuit 132. An output pulse generator 150 provides the pacing stimulus to the patient's heart 104 in response to a paced trigger signal developed by digital controller/timer circuit 132 each time the escape interval times out, or an externally transmitted pacing command has been received, or in response to other stored commands as is well known in the pacing art.

Digital controller/timer circuit 132 is coupled to a processing/amplifying circuit (ACTIVITY) 152 for receiving amplified and processed sensor output (Output$_{act}$) from sensor S$_1$ and associated ACTIVITY circuitry which is representative of activity. In a preferred embodiment of the present invention, pacemaker 100 is capable of operating in various non-rate-responsive modes which include VVI, VOO and VVT, as well as corresponding rate responsive modes of VVIR, VOOR and VVTR. Alternatively, the present invention may be implemented in a DDD/DDR pacing system where the PMT detection and recording features of the present invention may be implemented.

The system as described in FIG. 6 corresponds to a pacing system of a type described in U.S. patent application Ser. No. 567,476 filed Aug. 14, 1990, assigned to the assignee of the present invention and incorporated herein by reference. The system as envisaged in the context of the present invention includes the electrodes A, B and C coupled to the switching, signal processing and auto capture block 160 which is incorporated within the input/output circuit 112 and may include the far-field EGM recording system depicted in FIG. 5 as well as the auto capture circuitry and algorithm depicted in FIGS. 7 and 8. Furthermore, it is contemplated that the processed EGM signals may be automatically recorded on the occurrence of certain events, particularly in conjunction with a dual chamber pacing or arrhythmia control system, for initiating the recording of the far-field EGM in the presence of PMTs, high atrial or ventricular rates or the detection of any other form of arrhythmia. The switching, processing and auto capture block 160 may take the form of the circuits depicted in FIG. 7 (in conjunction with the algorithm of FIG. 8) and FIGS. 10, 11A–11C and 12A–12C.

Autocapture Detection—As described hereinbefore, the detection of the capture of the patient's heart following the delivery of a stimulating pulse by the pace out circuit 150 may be conducted by selecting the highest peak amplitude EGM signal picked up between the electrodes A-B and C-B. The highest amplitude far field EGM signal may be employed to detect the capture of the heart by the pacing output pulse periodically in conjunction with the sequential decrementing of the pacing output pulse width or amplitude until capture is lost in a manner well known in the prior art. After capture is lost, the output pulse energy may be incremented by a pre-set or percentage value.

Figure 7:
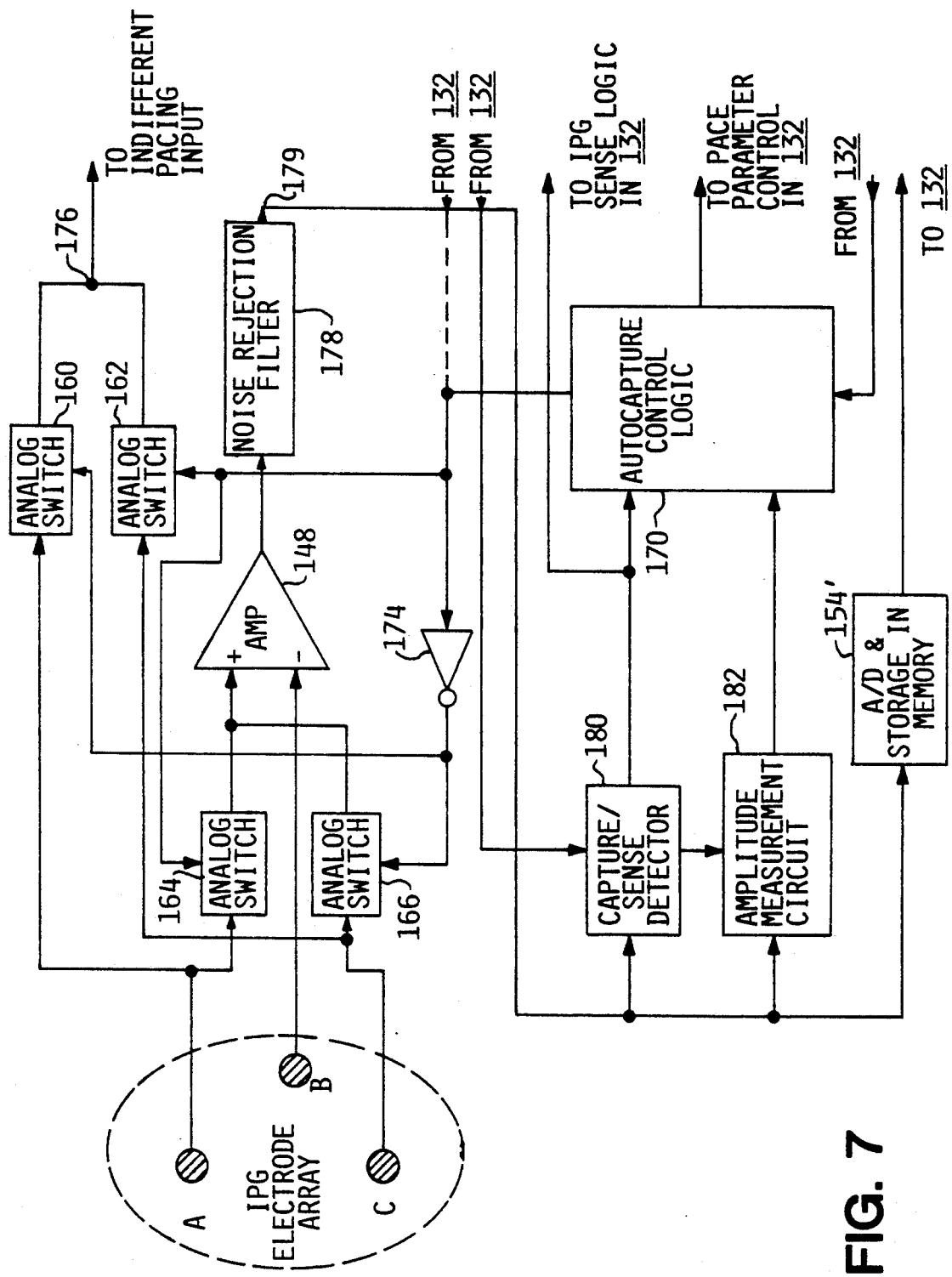
FIG. 7 is a simplified block diagram of a serial processing system for providing capture detection in the pacing system of FIG. 6.
Figure 8:
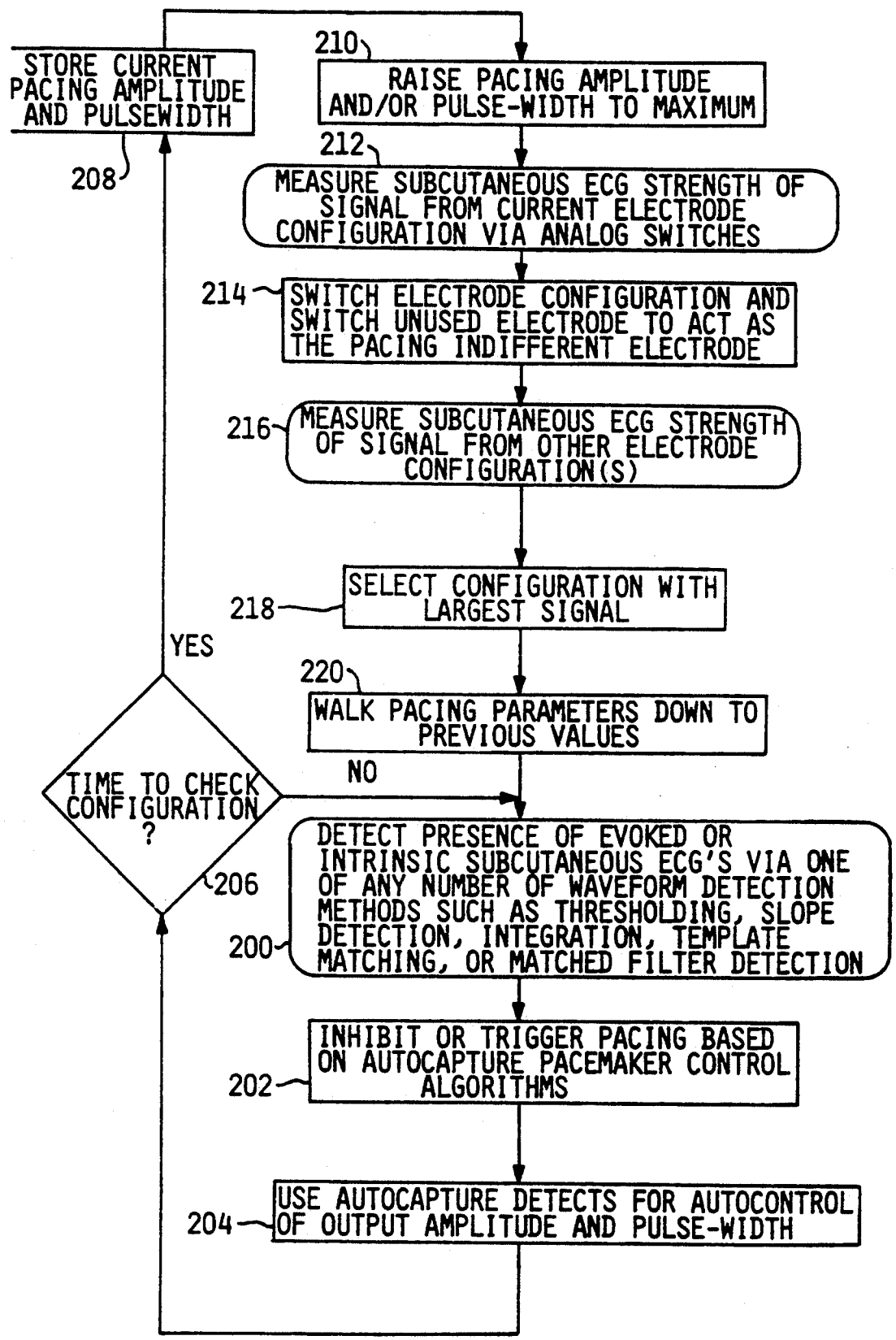
FIG. 8 is a flow chart of an algorithm for controlling the operation of the capture detection system of FIGS. 6 and 7.

A capture detection, threshold measurement and output pulse adjustment algorithm is depicted in the flow chart of FIG. 8. FIG. 7, taken in conjunction with FIG. 8, depicts a block diagram of a system for detecting capture and setting the pacing pulse parameters accordingly, as well as a system for selecting one of the unused electrodes A or C as the pacing indifferent electrode in unipolar pacing systems.

Turning now to FIG. 7, it depicts the selection of the electrode pair A-B or C-B providing the directional far field EGM having preferred characteristics for subsequent use as the capture detect (and signal storage) EGM path and the dedication of the unused electrode as the classic unipolar pace/sense indifferent electrode. In FIG. 7, the electrodes A, B and C are coupled to the block 160 of FIG. 7, and the output signals of block 160 are applied to the digital controller/timer circuit 132. Certain control signals are received from circuit 132 to enable periodic testing of the optimum electrode pair and capture detection.

In FIG. 7, the electrodes A, B and C are coupled to the inputs of analog switches 160, 162, 164 and 166 and the common electrode B is coupled to the negative input of the differential amplifier 148. The positive input of differential amplifier 148 is coupled to the output of analog switches 164 and 166 which are alternately selected by the autocapture logic 170. In effect, the autocapture logic 170, in response to command from the digital controller/timer circuit 132, provides a switch enable signal that is either a high or low binary signal to node 172. A high signal at 172 will be converted to a low signal by inverter 174 and applied to the switch control inputs of analog switches 160 and 166 to effectively open analog switches 160 and 166 to disconnect the electrode A from the node 176 and disconnect the electrode C from the positive input of differential amplifier 148. Simultaneously, the switches 162 and 164 are closed by the high switch enable signal, thus connecting the electrode C to the node 176 and the electrode A to the positive input of differential amplifier 148. Whichever one of the electrodes A and C that is connected to node 176 operates as the pace/sense indifferent electrode. In bipolar pacing systems having electrodes 103 and 105 on lead 102 of FIG. 6, it may be possible to program the pacing system to operate in either of the unipolar mode employing the electrodes A or C or the bipolar mode employing the ring electrode 105 as is well known in the prior art.

The output signal of the amplifier 148 is applied to the noise rejection band pass filter block 178 in order to filter out high and low frequency signal distortion induced by muscle noise and other artifacts. The output signal of the filter 178 is applied to the capture/sense detector 180 which may comprise a peak slope or amplitude threshold detector having programmable sensitivity threshold levels as is well known in the prior pacing art. The output signal of the capture/sense detector 180 is usually a fixed amplitude and duration pulse merely signifying the event detection. That sensed event signal may be applied directly to the digital controller/timer circuit 132 as well as to the autocapture logic 170.

The filtered directional electrogram signal may also be applied to the inputs of amplifier and signal processing block 182, as well as to the input of the analog to digital convertor and temporary buffer memory storage block 154 to develop the digitized data representing the sampled amplitudes of the filtered directional EMG for data storage in RAM of circuit 114 in the fashion described above in reference to FIG. 5. The system as described may also be implemented as components 30, 34, 38 and 40 of FIG. 5 for data storage.

Turning now to the algorithm depicted in the flow chart of FIG. 8 in conjunction with the block diagrams of FIGS. 6 and 7, the algorithm contemplates the continuous detection of the presence of evoked or intrinsic subcutaneous EGMs by one of any number of wave form detection methods, such as threshold detection, slope detection, integration, template matching or matched filter detection in block 200. Periodically, it is contemplated that the electrode selection will be rechecked to select the directional configuration that provides the highest peak amplitude (or other characteristic) for use in the normal operation of the pacing system.

Amplitude measurement block 182 is employed in connection with the autocapture logic 170 in the periodic checking of the peak amplitude of the directional EGM in the signal paths A-B and C-B. In this regard, the outputs of amplifier 182 are peak detected signals that are stored in buffers in autocapture logic 170 for comparison to one another. If the far-field EGM signal in the direction A-B has a greater peak amplitude than the far-field EGM signal in the direction C-B, then the autocapture logic 170 output signal at node 172 is high, and it closes switches 162 and 164. The high output signal is inverted by inverter 174 and operates to switch open analog switches 160 and 166. In this fashion the electrode C is connected to the positive input of the differential amplifier 148, and the electrode B is connected to the node 176 to act as the classic unipolar pace/sense indifferent electrode.

Thus in the normal sequence of pacing operation, the detected far-field EGM signal characteristic in block 200 is employed to inhibit or trigger pacing based on autocapture pacemaker control algorithms in block 202. The use of the autocapture detects for autocontrol of output amplitude and pulse width is effected in block 204. In regard to steps 202 and 204, suitable algorithms and circuitry for periodically determining the stimulation threshold and automatically setting the pacing pulse energy at a safety factor level above the determined stimulation threshold are set forth in the DeCote '376 and '508 patents incorporated herein by reference. This normal operating program loops back in block 206 to block 200 until the digital controller/timer circuit 132 provides a periodic checking signal to decision block 206. If the time flag is issued, then the program moves to the electrode selection algorithm comprising steps 208 to 220. At this time the autocapture control logic 170, the capture/sense detector 180 and the amplitude measurement circuit 182 of FIG. 7 are enabled by signals from digital controller/time circuit 132.

In step 208, the current pacing amplitude and pulse width is stored in temporary memory within the microcomputer circuit 114 and pacing amplitude and/or pulse width is increased to maximum output in block 210. Thereafter as one or more pacing pulses are delivered, the strength of the signal from the current electrode configuration is measured and stored in blocks 182 and 170 of FIG. 7. Thereafter, the electrode configuration is switched as described in reference to FIG. 7 and the EGM signal strength from the other electrode configuration or configurations is measured and stored. The two stored signal strengths are compared and the greater signal strength triggers the selection of the configuration that provides it as described above in conjunction with FIG. 8.

After selection of the new electrode configuration, the pacing parameters are decremented down to the previously stored values over a number of pacing cycles in step 220. Thereafter, the autocapture pacing control algorithms are repeated in steps 200-206 as previously described.

In a further embodiment of the autocapture detection algorithm and circuitry, it is contemplated that the far-field EGM signals sensed across the electrodes A-B and C-B may be combined in accordance with the parallel signal processing and combining circuit embodiments of FIGS. 10, 11A-11C and 12A-12C described hereinafter. In such systems, the steps 206 to 220 of the algorithm depicted in FIG. 8 would be unnecessary. All that would be necessary is that the autocapture function be periodically enabled in order to detect the threshold of capture. Alternatively, the autocapture function could be continuously enabled.

Figure 9:
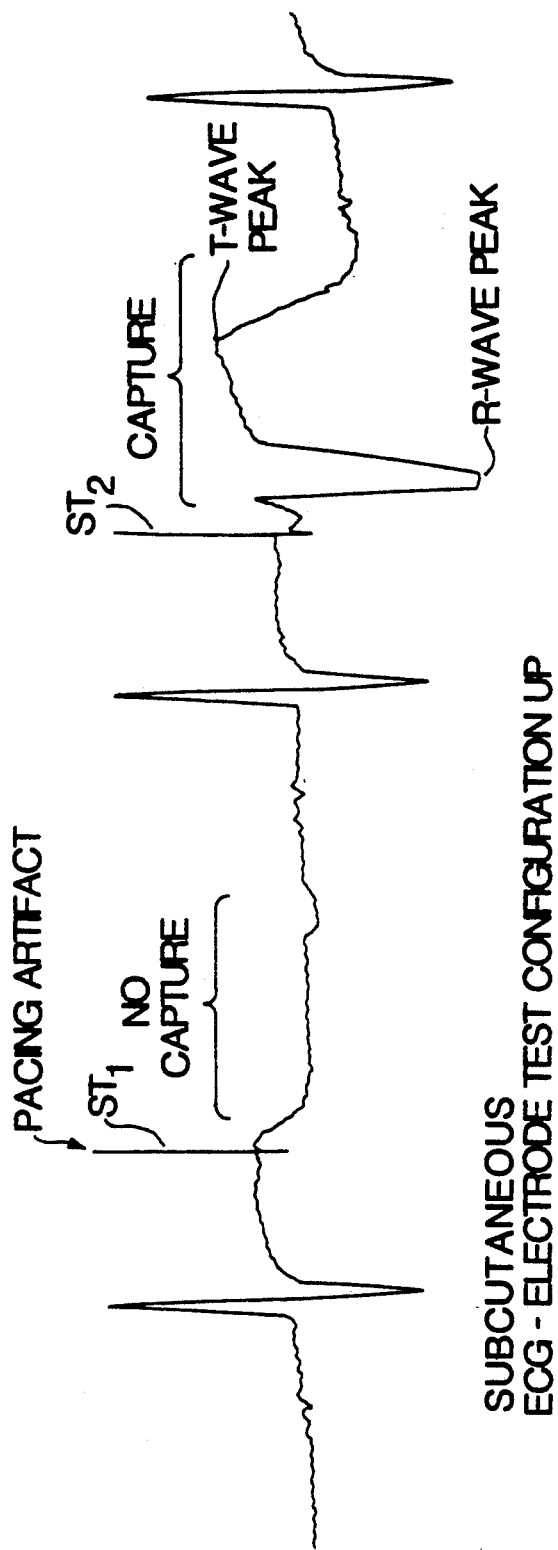
FIG. 9 is canine test data demonstrating the far-field EGM detection of capture across a single electrode pair.

Turning now to FIG. 9, it depicts the capture of a canine heart in response to a delivered stimulating pulse $ST_2$ in the righthand portion of the wave form. The morphology of the evoked QRS complex and the amplitude of the R-wave shows that it is relatively easy to peak amplitude detect the capture of the patient's heart.

The system depicted in FIGS. 6 and 7 may also be employed to determine the end of the refractory period of the heart following the delivery of a pacing pulse by monitoring the response of the heart to a sequence of paired stimulation pulses having time varying interpulse intervals in order to determine the minimum interval wherein the second pulse captures the heart. In reference to FIG. 9, it depicts the far field electrogram taken in a subcutaneous EGM capture test in a canine study wherein the pacing pulse $ST_1$ is delivered within the refractory period following the immediately preceding natural ventricular depolarization resulting in no capture of the heart. The pacing pulse $ST_2$, falling just outside the refractory interval results in capture of the heart. FIG. 9 thus illustrates the feasibility of capture detection in general by virtue of the relatively large magnitude driven QRS complex picked up by the far field EGM in relation to the naturally occurring R wave and the pacing artifact as well as the feasibility of determining the refractory interval.

FIG. 9 also illustrates the feasibility of measuring the Q-T time interval or other characteristics of the spontaneous and driven QRST complex for developing a control signal for rate responsive pacemakers. In particular, the interval from the delivery of the stimulating pulse $ST_2$ to the peak of the T-wave may be measured, and a pacing rate control signal may be derived as described in the Callaghan '610 patent and the Rickards '803 patent referenced above.

Figure 10:
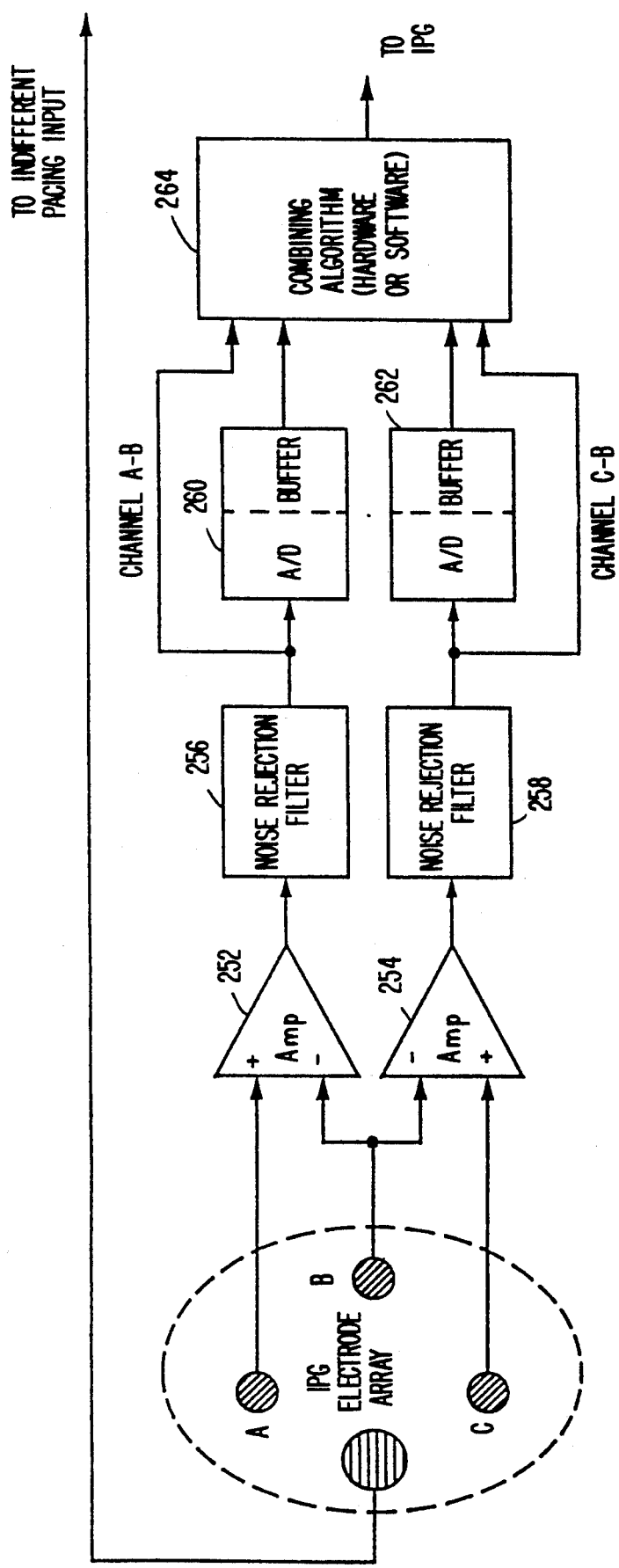
FIG. 10 is a simplified block diagram of a parallel signal processing circuit for combining the EGM signal magnitudes detected across orthogonal electrode pairs A-B and C-B in conjunction with one of the circuits in algorithms of FIGS. 11A-11C or 12A-12C usable in the systems of FIGS. 5 and 6.

Parallel Signal Processing—Turning now to FIG. 10, it shows a parallel signal processing circuit including amplifiers 252, 254, noise rejection filters 256, 258 and A/D converters/buffers 260, 262 for digitizing and storing temporarily the digitized values of the A-B and B-C channel EGM signal magnitudes for processing in the combining algorithm block 264 when digital signal processing is employed.

Figure 11A:
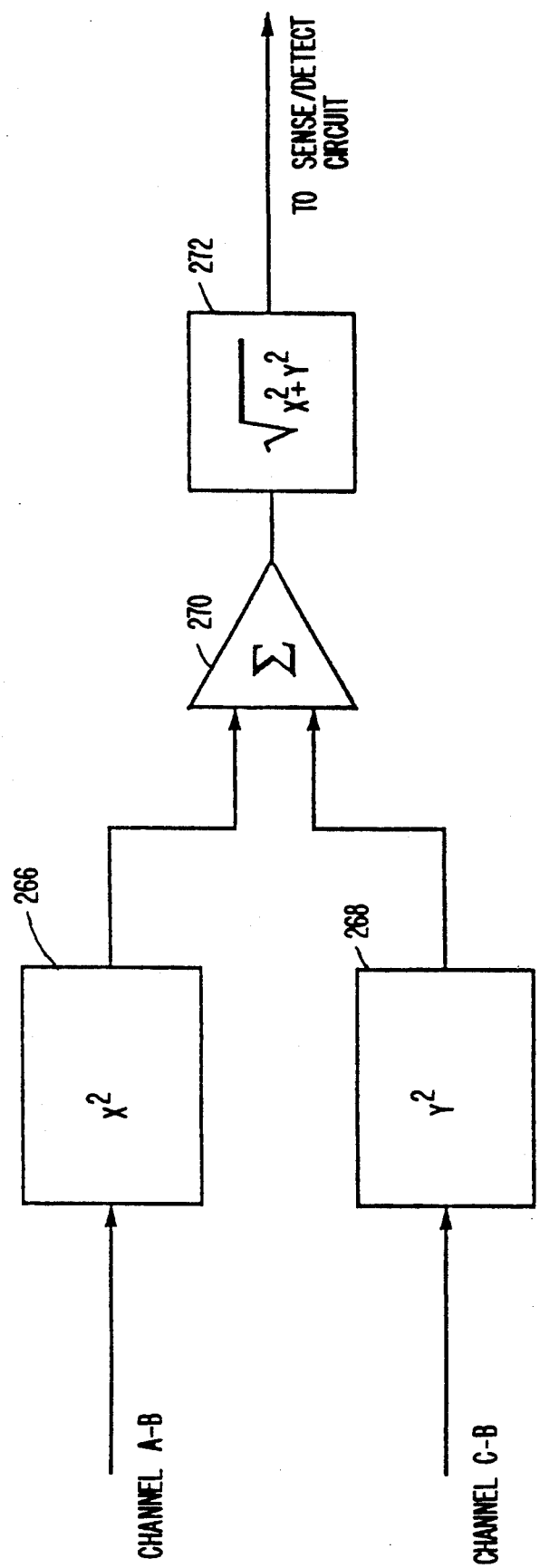
FIGS. 11A-11C are alternate embodiments of nonlinear signal combining circuits/algorithms usable in the parallel signal processing circuits of FIG. 10 and the systems of FIG. 6.

The combining algorithm block 264 may be implemented in hardware or software and take the form of the signal processing block diagrams of FIGS. 11A–11C and 12A–12C. FIG. 11A depicts a nonlinear combining circuit wherein the square root of the sum of the squared X and Y values is derived. The X value from channel A-B of block 256 (FIG. 10) and the Y value from block 258 (FIG. 10) are squared in blocks 266, 268 and summed in summing amplifier 270. The square root of the summed $X^2 + y^2$ value is derived in block 272.

Figure 11B:
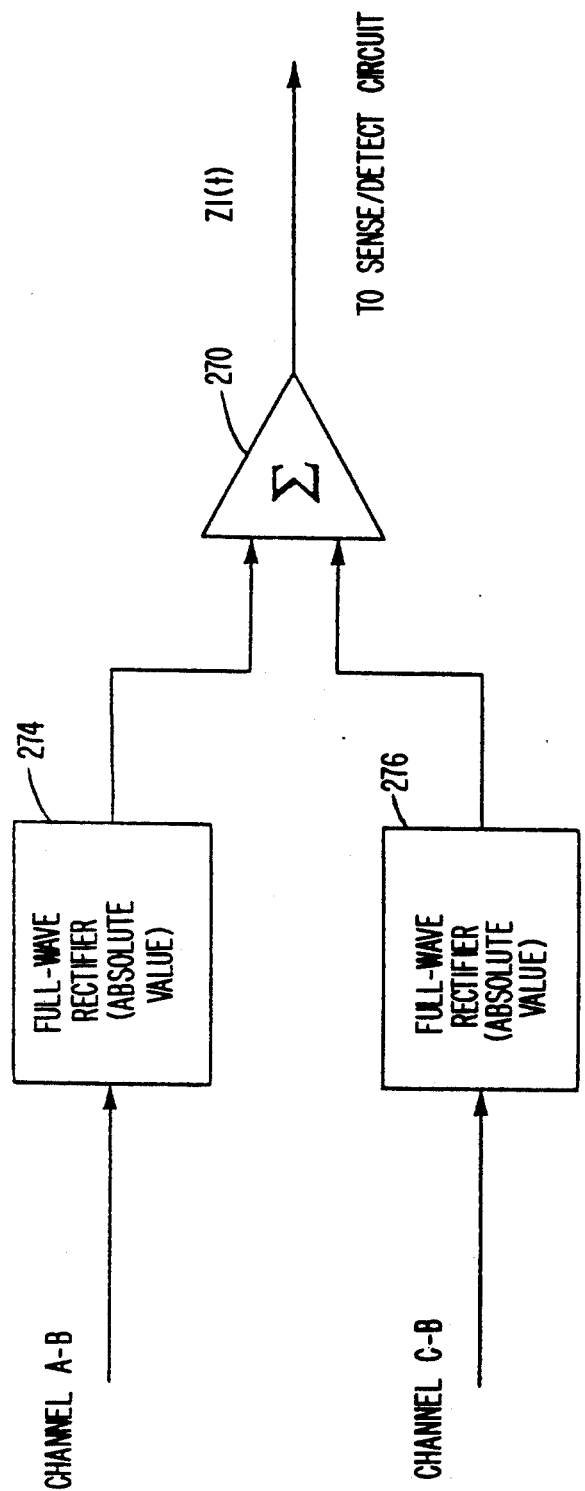

FIG. 11B depicts a nonlinear combining circuit using the absolute value of the channel A-B and B-C EGM signal magnitudes as a first approximation of orientation independent signal. In this system, the magnitude of the signal on channel A-B and C-B are absolute value converted in blocks 274 and 276 and summed in summing amplifier 278.

Figure 11C:
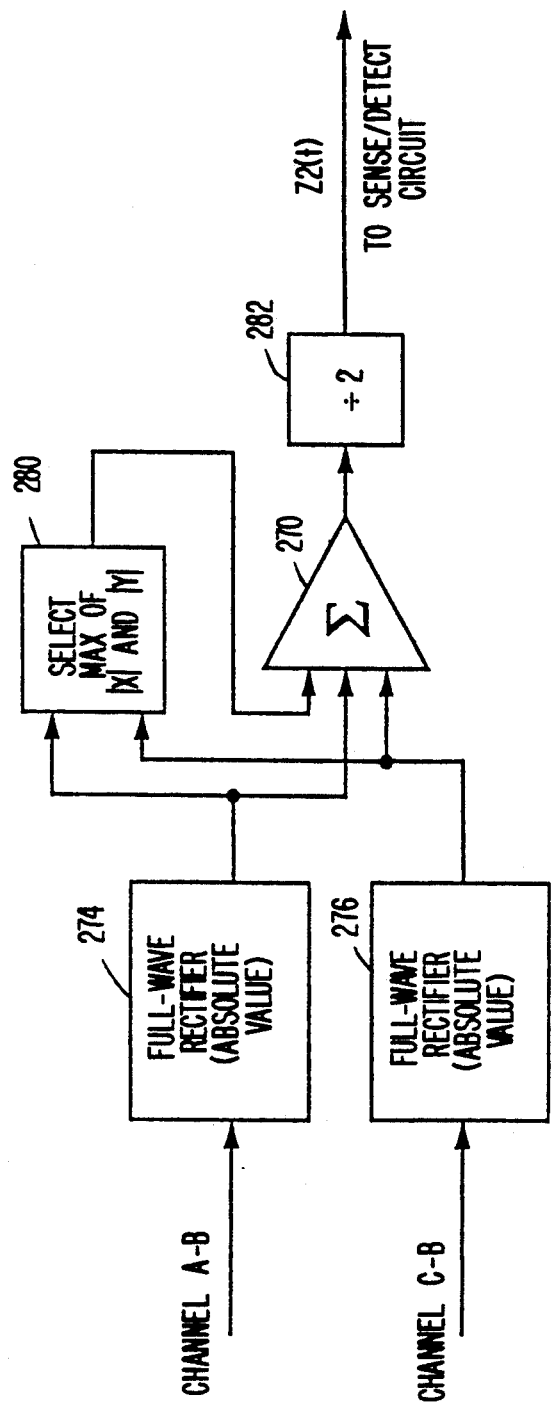

In FIG. 11C, a further approximation approach for the nonlinear combination of the far-field EGM signal magnitudes on channels A-B and B-C is depicted. In this embodiment, the full wave rectified signals are compared to select the maximum absolute value signal in block 280 and that maximum signal is summed together with the time varying EGM signal in summing amplifier 270. The resulting summed signal is divided by 2 in block 282 to provide the second approximation of an orientation independent signal.

These nonlinear approximations are sufficient for use in capture detection and employ the analog channel A-B and C-B signal values applied directly to the combining algorithm block 264 of FIG. 10. In this situation there is no need to digitize the signal inasmuch as the only signal being sought is a detectable triggering signal from the far-field EGM.

Figure 12A:
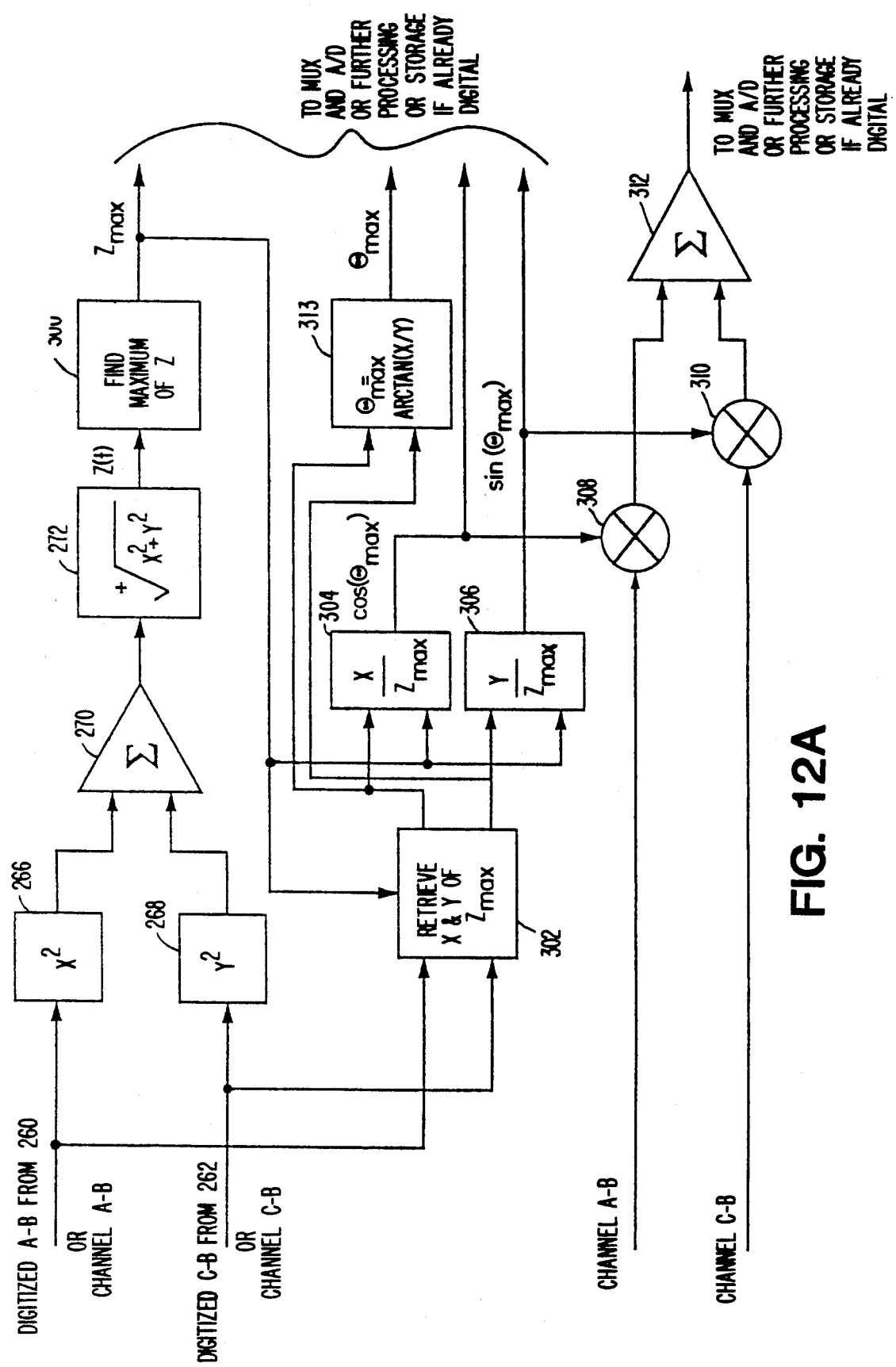
FIGS. 12A-12C are alternate embodiments of linear signal combining circuits/algorithms usable in the parallel signal processing circuits of FIG. 10 and the systems of FIGS. 5 and 6.
Figure 12B:
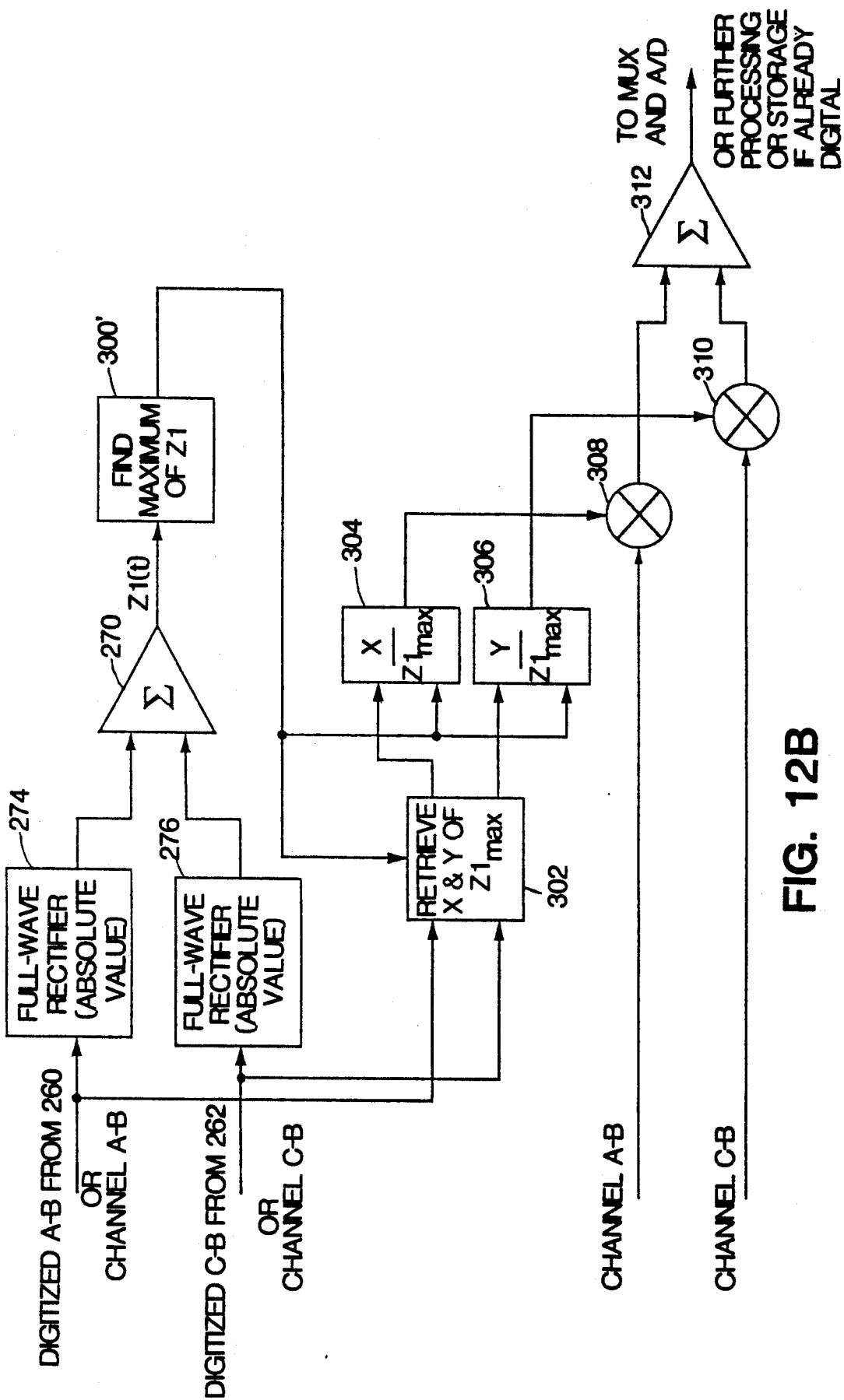
Figure 12C:
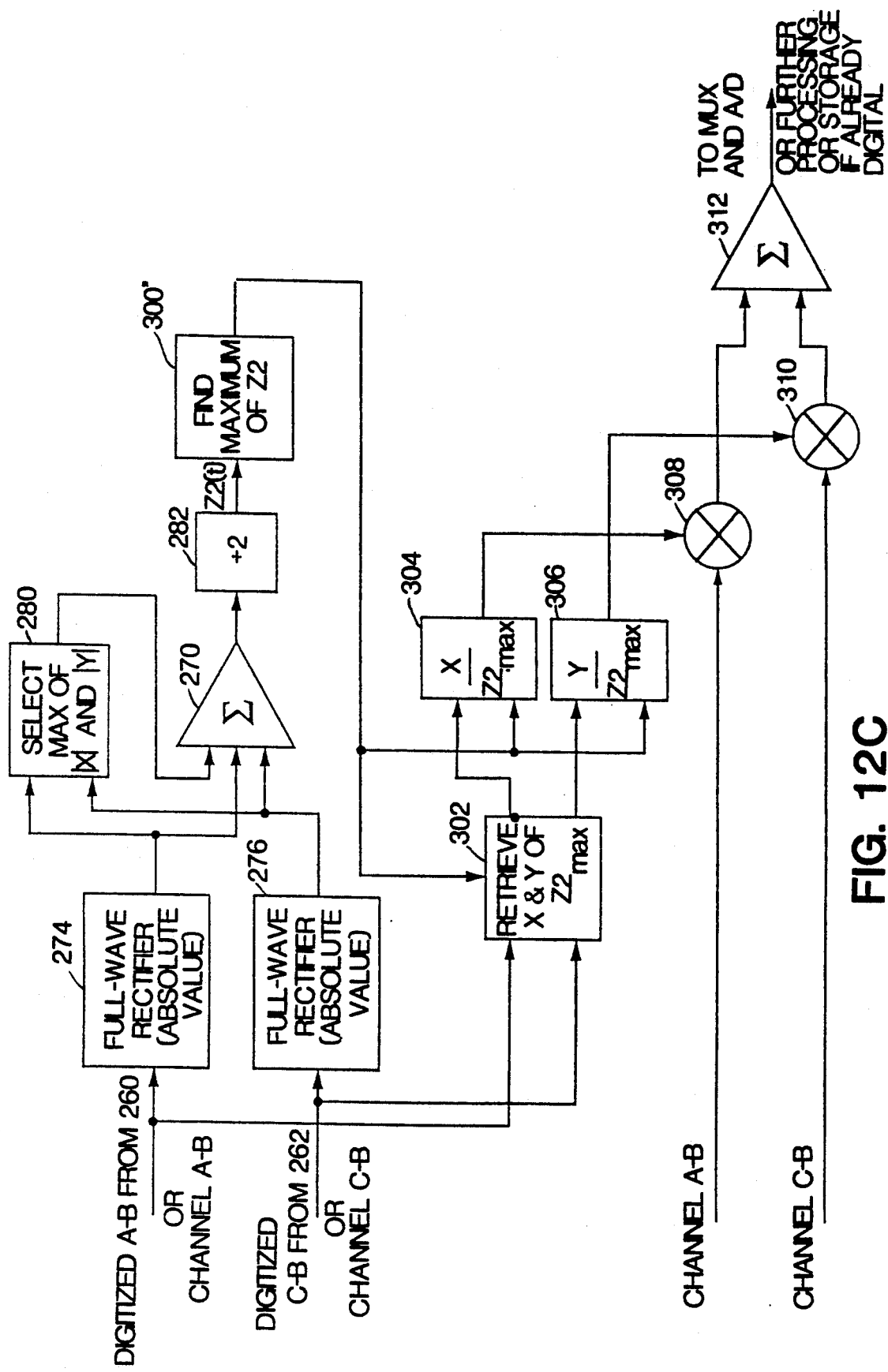

Turning now to FIGS. 12A–12C, the digitized values of the far-field EGM magnitude sensed across the electrode pairs A-B and C-B are combined in linear signal processing circuitry that effects a maximum signal axis rotation.

The vector $(2t)$ magnitude is first determined and then the maximum of this vector magnitude is identified via search and comparison methods (either digital or analog means can be employed). The associated instantaneous values of the two orthogonal channels, x(t) and y(t) corresponding to channels A-B and C-B can then be used to find the rotational factors, cos(Omax), and sin-(Omax). The signal equivalent to that which would be present from a pair of electrodes aligned with the principal cardiac vector can then be obtained per FIG. 12A by multiplying the derived rotational factors by the signals from the orthogonal channels and then adding them. By periodically recalculating the rotational factors in this implementation to compensate for rotation of either the electrode axis or the principal cardiac vector, the output signal from this implementation will always be the maximum possible, and will be completely rotation insensitive. This signal can then be used to provide a reliable and optimal signal for the applications discussed above. Note that two approximate and less calculation intensive methods for calculating the vector magnitude whose means are described in the rotation compensation approaches of FIGS. 12B and 12C.

The principal cardiac vector magnitude and phase (orientation angle), can also be used as a diagnostic tool to the physician (and could be measured by the means described in reference to FIGS. 12A–12C if the implanted device is fixed in position by sutures or other means) (since it provides them with information regarding the principal depolarization direction of the heart which can relate to different disease conditions), and can appropriately be stored for later retrieval. The orientation (angle) can be computed per FIG. 12A by calculating the arctangent of x/y associated with the principal cardiac vector magnitude.

In addition, if the implanted device is fixed in position by sutures or other means, the dynamic (time-varying) vector electrogram, z(t), may also be useful as a diagnostic tool, since it provides the physician with a means for visualizing the dynamic changes in orientation and magnitude of the electric field due to the distinctive time, magnitude, and orientation pattern of depolarization which occurs in the heart. This information may also be indicative and descriptive of different conditions, or different states of the heart.

FIGS. 12A–12C employ the nonlinear vector magnitude combining circuitry of FIGS. 11A–11C, respectively, but employ the digitized input signals from buffers 260 and 262 of FIG. 10 for the channel A-B and B-C digitized signal values. In each of FIGS. 12A–12C, the maximum vector value is determined in block 300. The corresponding X and Y values stored in buffers 260 and 262 are retrieved in block 302 to be employed to develop multiplication factors which relate to the angular deviation of the maximum signal value vector from the abscissa and ordinate directions defined by the electrode pairs A-B and C-B as described hereinbefore in conjunction with FIGS. 3A–3C and 4A–4C.

Because the electrode array is fixed and the angular deviation from the fixed abscissa and ordinate varies with the direction of the depolarization wave traveling through the heart (as shown in FIG. 1) there is one angular deviation at which the vector magnitude is greatest as also shown in the vectors of FIGS. 4A–4C. The maximum signal axis rotation can be mathematically rotated as given by equations for example in *College Calculus With Analytic Geometry*, pp. 320–321, by Protter & Morrey, Addison & Wesley Publishing Company, Inc., copyright 1970. The exact version of the linear combiner with maximum signal axis rotation is depicted in FIG. 12A and first and second approximations of the maximum signal axis rotation linear combiner network are shown in FIGS. 12B and 12C.

In each case, the values retrieved in block 302 are separately applied to divider blocks 304 and 306 which produce the multiplier values that are applied to multiplier circuits 308 and 310. The multiplier circuits 308 and 310 receive the channel A-B and channel C-B far-field electrogram signal values, multiply those values by the multiplier factors and apply the multiplied values to the summing amplifier 312 thus the summing amplifier 312 presents a set of sampled and digitized vector EGM values reflecting the actual maximum magnitude of the electric field in response of the electrode array, regardless of the orientation of the fixed electrode array to the principal cardiac vector.

As described above, each of the circuits of FIGS. 10, 11A-11C or 12A-12C may be combined and employed with the signal recording and therapy delivering medical devices identified above.

The advantages and disadvantages of the selective serial signal processing (FIG. 7) and parallel signal processing (FIGS. 10, 11A-11C, 12A-12C) approaches can be summarized as follows:

Serial approach
requires little post-processing
requires optimization test mode
does not provide optimal signal (only 70% of max in worst case)
can be used in applications
Parallel linear approach
requires additional post-processing
does not require test mode except to identify maximal vector angle
provides most optimal signal strength
can be used in all applications
Parallel nonlinear approach
requires additional post-processing
never requires test mode
provides most optimal signal strength
provides event detection for capture
detection, Q-T interval measurement, rate determination
does not provide good signal for storing morphology of PQRST complex Experimental Results—The feasibility of detecting the EGM from closely spaced electrodes of the type depicted hereinbefore was confirmed by conducting a clinical study of 11 patients undergoing pacemaker implantation. In those patients, a prototype containing four disc shaped titanium electrodes, each 0.21 inches in diameter, arranged in a square configuration spaced 0.72 inches center to center, was constructed on an epoxy substrate. The epoxy substrate containing the four disc electrodes and a connector block for leads leading from the substrate was temporarily placed face down in the subcutaneous pocket in the left pectoral region of the 11 patients. Bipolar recordings were made from a horizontal pair, a vertical pair and both diagonal pairs of electrodes (inter-electrode distance of 1.02 inches) and recorded on magnetic tape after filtering at 0.5 to 250 Hz. The mean peak-to-peak amplitude in each configuration was determined over a five beat interval.

Clear recordings were obtained from all 11 patients with recognizable P, QRS and T waves. The amplitude of the diagonal bipolar electrograms (195 plus or minus 45 microvolts and 184 plus or minus 61 microvolts) tended to be higher than recordings from either the vertical pair (154 plus or minus 67 microvolts) or the horizontal pair (123 plus or minus 57 microvolts, P less than 0.05 compared to diagonal pairs). The maximum amplitude recorded from any configuration was 214 plus or minus 41 microvolts. These results demonstrate that an implantable arrhythmia monitor is able to record adequate signals from a one inch square device. It was concluded that further work was required to assess long-term stability of recordings and the effects of myopotentials. Subsequent canine studies have established that the effect of myopotentials may be alleviated by placing the electrode array face up, that is against the patient's skin, rather than face down against the pectoral muscles.

Thus, it has been shown that the far-field EGM signal developed from the subcutaneous electrode arrays and circuitry described above may be sensed without encountering polarization effects and employed in a variety of contexts to record EGM related data and to develop system control signals automatically or upon command.

While the invention has been described above in connection with the particular embodiments and examples, one skilled the art will appreciate that the invention is not necessary so limited. It will thus be understood that numerous other embodiments, examples, uses, modifications of, and departures from the teachings disclosed may be made, without departing from the scope of the present invention as claimed herein.

We claim:

1. An apparatus for monitoring cardiac signals, comprising:
   a hermetically sealed housing;
   first and second pairs of electrodes mounted to said housing;
   sensing means, located within said housing, for sensing cardiac signals;
   command means, located outside said housing, for providing command signals indicative of which of said first and second electrode pairs are to be coupled to said sensing means;
   selecting means, located within said housing and responsive to said command signals, for selectively coupling said first and second electrode pairs to said sensing means;
   processing means, located within said housing, for processing and converting said sensed cardiac signals into data signals; and
   means for storing said data signals.

2. An apparatus for monitoring cardiac signals, comprising:
   a hermetically sealed housing;
   first and second pairs of electrodes mounted to said housing;
   sensing means, located within said housing, for sensing cardiac signals;
   command means, located outside said housing, for providing command signals indicative of which of said first and second electrode pairs are to be coupled to said sensing means;
   selecting means, located within said housing and responsive to said command signals, for selectively coupling said first and second electrode pairs to said sensing means;
   means for defining operational parameters of said apparatus;
   means for processing and converting said sensed cardiac signals into a control signal; and
   means responsive to said control signal for altering a said operational parameter of said apparatus.

3. An apparatus for monitoring cardiac signals, comprising:
   a hermetically sealed housing;

first and second pairs of electrodes mounted to said housing;

sensing means, located within said housing, for sensing cardiac signals;

command means, located outside said housing, for providing command signals indicative of which of said first and second electrode pairs are to be coupled to said sensing means;

selecting means, located within said housing and responsive to said command signals, for selectively coupling said first and second electrode pairs to said sensing means; and transmitter means for transmitting said sensed cardiac signals from said housing.

4. An apparatus according to claim 1 or claim 2 or claim 3 further comprising:

means for generating a store command; and means responsive to said store command for storing said sensed cardiac signals.

5. An apparatus according to claim 4 wherein said store command generating means comprises means responsive to said sensed cardiac signals, for generating said store command in response to the occurrence of sensed cardiac signals.

6. An apparatus according to claim 4 wherein said store command generating means comprises a transmitter means external to said housing, for transmitting said store command to said responsive means.

7. An apparatus for monitoring cardiac signals, comprising:

a hermetically sealed housing;

first and second pairs of electrodes mounted to said housing;

sensing means, located within said housing, for sensing cardiac signals and for generating output signals corresponding to said sensed cardiac signals;

selecting means, located within said housing, for selectively coupling said first and second electrode pairs to said sensing means;

means for defining a preferred cardiac signal;

means for comparing said output signals generated when said sensing means is coupled to said first electrode pair to said output signals generated when said sensing means is coupled to said second electrode pair to determine which of said first and second electrode pairs produces said preferred cardiac signal;

control means, responsive to said comparing means, for controlling said selecting means to couple said sensing means to the one of said first and second electrode pairs which produces said preferred cardiac signal;

processing means, located within said housing, for processing and converting said output signals into data signals; and means for storing said data signals.

8. An apparatus for monitoring cardiac signals, comprising:

a hermetically sealed housing;

first and second pairs of electrodes mounted to said housing;

sensing means, located within said housing, for sensing cardiac signals and for generating output signals corresponding to said sensed cardiac signals;

selecting means, located within said housing, for selectively coupling said first and second electrode pairs to said sensing means;

means for defining a preferred cardiac signal;

means for comparing said output signals generated when said sensing means is coupled to said first electrode pair to said output signals generated when said sensing means is coupled to said second electrode pair to determine which of said first and second electrode pairs produces said preferred cardiac signal; and control means, responsive to said comparing means, for controlling said selecting means to couple said sensing means to the one of said first and second electrode pairs which produces said preferred cardiac signal means for defining operational parameters of said apparatus;

means for processing and converting said output signals into a control signal; and means responsive to said control signal for altering a said operational parameter of said apparatus.

9. An apparatus for monitoring cardiac signals, comprising:

a hermetically sealed housing;

first and second pairs of electrodes mounted to said housing;

sensing means, located within said housing, for sensing cardiac signals and for generating output signals corresponding to said sensed cardiac signals;

selecting means, located within said housing, for selectively coupling said first and second electrode pairs to said sensing means;

means for defining a preferred cardiac signal;

means for comparing said output signals generated when said sensing means is coupled to said first electrode pair to said output signals generated when said sensing means is coupled to said second electrode pair to determine which of said first and second electrode pairs produces said preferred cardiac signal;

control means, responsive to said comparing means, for controlling said selecting means to couple said sensing means to the one of said first and second electrode pairs which produces said preferred cardiac signal; and transmitter means for transmitting said output signals from said housing.

10. An apparatus for monitoring cardiac signals, comprising:

a hermetically sealed housing;

first and second electrode pairs mounted to said housing;

sensing means coupled to said first and second electrode pairs for sensing cardiac signals from said first and second electrode pairs and for generating first and second output signals corresponding to cardiac signals sensed from said first and second electrode pairs, respectively; and signal processing means coupled to said sensing means for combining said first and second output signals to provide combined output signals; and means for storing said combined output signals.

11. An apparatus for monitoring heart signals, comprising:

a hermetically sealed housing;

first and second electrode pairs mounted to said housing;

sensing means coupled to said first and second electrode pairs for sensing cardiac signals from said first and second electrode pairs and for generating first and second output signals corresponding to cardiac signals sensed from said first and second electrode pairs, respectively; and signal processing means coupled to said sensing means for combining said first and second output signals to provide combined output signals;

means for defining operational parameters of said apparatus;

means for processing and converting said combined output signals into a control signal; and means responsive to said control signal for altering a said operational parameter of said apparatus.

12. An apparatus for monitoring cardiac signals, comprising;

a hermetically sealed housing;

first and second electrode pairs mounted to said housing;

sensing means coupled to said first and second electrode pairs for sensing cardiac signals from said first and second electrode pairs and for generating first and second output signals corresponding to cardiac signals sensed from said first and second electrode pairs, respectively; and signal processing means coupled to said sensing means for combining said first and second output signals to provide combined output signals; and transmitter means for transmitting said combined output signals from said housing.

13. An apparatus according to claim 10 or claim 11 or claim 12 wherein said combining means comprises means for combining said first and second output signals to derive directional vectors and means for providing combined output signals which comprise magnitudes of said directional vectors.

14. An apparatus according to claim 10 or claim 11 or claim 12 wherein said combining means comprises means for combining said first and second output signals to derive directional vectors and means for providing combined output signals which comprise magnitudes and directions of said directional vectors.

15. An apparatus according to claim 1 or claim 2 or claim 3 or claim 7 or claim 8 or claim 9 or claim 10 or claim 11 or claim 12, wherein at least one of said first and second electrode pairs comprises an electrode means adjacent to said housing, for location in subcutaneous tissue, mounted to said housing by means of an electrical lead extending from said housing.

16. A pacemaker according to claim 15 wherein said responsive means comprises means for defining a preferred cardiac signal and means for determining which of said first and second electrode paris provides said preferred cardiac signal and selecting means responsive to said determining means for selectively coupling one of said first and second electrode pairs of said sensing means for subsequent use in detecting capture of said patient's heart.

17. A method of monitoring cardiac signals, comprising:

implanting in a patient an apparatus comprising a hermetically sealed housing, first and second pairs of electrodes mounted to said housing, a sensing means located within said housing for sensing cardiac signals and selecting means located within said housing and responsive to command signals for selectively coupling said first and second electrode pairs to said sensing means, such that said housing and said first and second electrode pairs are located outside of said patient's heart in the subcutaneous tissue of said patient;

transmitting a said command signal indicative of which of said first and second electrode pairs are to be coupled to said sensing means to said apparatus from outside of said housing; and subsequently employing said coupled electrode pair to monitor said cardiac signals.

18. A method according to claim 17 further comprising:

processing and converting said sensed cardiac signals into data signals; and storing said data signals.

19. A method according to claim 18 further comprising transmitting said sensed cardiac signals from said housing.

20. A method according to claim 17, further comprising:

defining operational parameters for said apparatus;

processing and converting said sensed cardiac signals into a control signal; and employing said control signal to alter a said operational parameter of said apparatus.

21. A method of monitoring cardiac signals, comprising:

defining a preferred cardiac signal;

implanting in a patient a device comprising a hermetically sealed housing, first and second pairs of electrodes mounted to said housing, a sensing means located within said housing for sensing cardiac signals and for generating output signals corresponding to said sensed cardiac signals and selecting means located within said housing for selectively coupling said first and second electrode pairs to said sensing means; such that said housing and said first and second electrode pairs are located outside of said patient's heart in subcutaneous tissue of said patient;

selectively coupling said sensing means to said first and second electrode pairs;

comparing said output signals generated when said sensing means is coupled to said first electrode pair to said output signals generated when said sensing means is coupled to said second electrode pair to determine which of said first and second electrode pairs produces said preferred cardiac signal;

employing said selecting means to couple said sensing means to the one of said first and second electrode pairs which produces said preferred cardiac signal; and subsequently employing said one of said first and second electrode pairs which produces said preferred cardiac signal to monitor said cardiac signals.

22. A method according to claim 21 further comprising:

processing and converting said sensed cardiac signals into data signals; and storing said data signals.

23. A method according to claim 21, further comprising:

defining operational parameters for said apparatus;

processing and converting said sensed cardiac signals into a control signal; and employing said control signal to alter a said operational parameter of said apparatus.

24. A method according to claim 21 further comprising transmitting said sensed cardiac signals from said housing.

25. A method of monitoring cardiac signals, comprising:
   implanting in a patient an apparatus comprising a hermetically sealed housing, first and second electrode pairs mounted to said housing and sensing means located within said housing coupled to said first and second electrode pairs for sensing cardiac signals from said first and second electrode pairs and for generating first and second output signals corresponding to cardiac signals sensed from said first and second electrode pairs, respectively, such that said housing and said first and second electrode pairs are located outside of said patient's heart in subcutaneous tissue of said patient;
   combining said first and second output signals to provide combined output signals; and
   employing said combined output signals to monitor the heart activity of said patient.

26. A method according to claim 25 wherein said combining step comprises combining said first and second output signals to derive directional vectors and providing combined output signals which comprise magnitudes of said directional vectors.

27. A method according to claim 25 wherein said combining step comprises combining said first and second output signals to derive directional vectors and providing combined output signals which comprise magnitudes and directions of said directional vectors.

28. A method according to claim 17 or claim 21 or claim 25, wherein said step of implanting said apparatus comprises implanting at least one of said first and second electrode pairs having an electrode located adjacent to said housing, in said subcutaneous tissue, mounted to said housing by means of an electrical lead extending from said housing.

29. In an implantable cardiac pacemaker having pulse generator means for providing pacing pulses to cardiac tissue, output energy setting means for setting the energy of the applied pacing pulses and apparatus for detecting capture of a patient's heart by the applied pacing pulses, said capture detecting apparatus comprising means for sensing cardiac signals closely following said applied pacing pulses, the improvement wherein:
   said apparatus for detecting capture of the patient's heart comprises first and second electrode pairs, sensing means coupled to said first and second pairs of electrodes for sensing cardiac signals applied thereto and means responsive to said sensed cardiac signals from both said first and second electrode pairs for detecting capture of said patient's heart.

* * * * *